(12) United States Patent  
Bedwell et al.

(10) Patent No.: US 9,259,513 B2  
(45) Date of Patent: Feb. 16, 2016

(54) PHOTOCATALYTIC DISINFECTION OF IMPLANTED CATHETERS

(75) Inventors: William Bedwell, Palo Alto, CA (US);
Lorenza Moro, Palo Alto, CA (US);
Eric A. Arons, San Francisco, CA (US);
Pablo E. Garcia, Menlo Park, CA (US);
Osita Onugha, Santa Clara, CA (US);
Sanjeev Dutta, Los Altos, CA (US);
Sarah Young, Menlo Park, CA (US);
Karen F. Shakespear, San Francisco, CA (US); Janus A. J. Haagensen, Menlo Park, CA (US)

(73) Assignee: SRI INTERNATIONAL, Menlo Park ( * ) Notice: Subject to any disclaimer, the term of this patent is extended or adjusted under 35 U.S.C. 154(b) by 773 days.

(21) Appl. No.: 13/528,765

(22) Filed: Jun. 20, 2012

(65) Prior Publication Data

US 2013/0060188 A1    Mar. 7, 2013

Related U.S. Application Data

(60) Provisional application No. 61/499,056, filed on Jun. 20, 2011.

(51) Int. Cl.
*A61M 25/00*  (2006.01)
*A61L 29/10*  (2006.01)
(Continued)

(52) U.S. Cl.
CPC ............ *A61L 29/106* (2013.01); *A61L 2/0047* (2013.01); *A61L 29/14* (2013.01); *A61M 25/005* (2013.01); *A61M 25/0017* (2013.01); *A61M 25/0045* (2013.01); *A61L 2202/24* (2013.01); *A61M 2025/0056* (2013.01)

(58) Field of Classification Search
CPC .... A61M 25/00; A61M 37/00; A61L 29/106; A61L 2/0047; A61L 29/14
USPC ................................................ 604/21; 422/24
See application file for complete search history.

(56) References Cited

U.S. PATENT DOCUMENTS

| 5,312,813 A | 5/1994 | Costerton et al. |
| 5,328,451 A | 7/1994 | Davis et al. |

(Continued)

FOREIGN PATENT DOCUMENTS

| EP | 1291033 | 3/2003 |
| EP | 2161040 | 3/2010 |
| WO | WO 98/31420 | 7/1998 |

OTHER PUBLICATIONS

Del Pozo (Jan. 2009), "The Electricidal Effect: Reduction of *Staphylococcus* and Pseudomonas Biofilms by Prolonged Exposure to Low-Intensity Electrical Current,".

(Continued)

*Primary Examiner* — Sean E Conley
(74) *Attorney, Agent, or Firm* — Richard Aron Osman

(57) ABSTRACT

An implantable catheter is provided that may be disinfected without removal from the body of a patient, using a photocatalytic method to activate a reaction on the catheter surface that generates oxidizing agents in the form of Reactive Oxygen Species ("ROS") and thus destroy microorganisms in a biofilm that is present or forming. A catheter system includes the implantable catheter, a light source, and a source of power operably connected to the light source. Methods are also provided for disinfecting the implantable catheter in vivo.

63 Claims, 12 Drawing Sheets
(6 of 12 Drawing Sheet(s) Filed in Color)

(51) Int. Cl.
*A61L 2/00* (2006.01)
*A61L 29/14* (2006.01)

(56) References Cited

U.S. PATENT DOCUMENTS

| | | | |
|---|---|---|---|
| 5,409,467 A | 4/1995 | Raad | |
| 5,462,644 A | 10/1995 | Woodson | |
| 5,695,482 A | 12/1997 | Kaldany | |
| 5,779,912 A | 7/1998 | Gonzalez-Martin et al. | |
| 5,879,342 A | 3/1999 | Kelley | |
| 6,004,438 A | 12/1999 | Woodson | |
| 6,027,476 A | 2/2000 | Sterman | |
| 6,258,249 B1 | 7/2001 | Simpson | |
| 6,366,807 B1 | 4/2002 | Kosiba et al. | |
| 7,621,929 B2 | 11/2009 | Nita | |
| 7,744,555 B2 | 6/2010 | DiMauro et al. | |
| 8,233,957 B2 | 7/2012 | Merz et al. | |
| 8,267,883 B2 | 9/2012 | DiMauro et al. | |
| 2003/0125679 A1 | 7/2003 | Kubota et al. | |
| 2005/0175658 A1 | 8/2005 | Demauro et al. | |
| 2006/0004317 A1 | 1/2006 | Mauge et al. | |
| 2007/0279839 A1 | 12/2007 | Miller | |
| 2008/0140052 A1 | 6/2008 | Moller | |
| 2010/0010327 A1 | 1/2010 | Merz | |
| 2010/0087788 A1 | 4/2010 | Rosenblatt | |
| 2010/0233021 A1 | 9/2010 | Sliwa | |
| 2010/0256607 A1 | 10/2010 | Burnett | |
| 2010/0317948 A1 | 12/2010 | DiMauro | |
| 2011/0053144 A1 | 3/2011 | Garcia Alijaro et al. | |

OTHER PUBLICATIONS

Antimicrobial Agents and Chemotherapy, pp. 41-45.

Donlan (Mar. 1, 2001), "Biofilms and Device Associated Infections," Emerging Infectious Diseases 7(2).

Dunlop et al., "Detection and Removal of Pathogenic Biofilms on Medical Implant Surfaces," Personalised Health Management Systems, C.D. Nugent et al., Eds.

Elliott (2000), "Intravascular Catheter-Related Sepsis—Novel Methods of Prevention," Intensive Care Med. 26:S45-S50.

Ganesh et al. (2008), "Fiber-Optic Sensors for the Estimation of Oxygen Gradients within Biofilms on Metals," Optics and Lasers in Engineering 46:3217-327.

Liu et al. (1993), "The Effects of Electric Current on Bacteria Colonising Intravenous Catheters," Journal of Infection 27:261-269.

Ohko et al. (2001) "Self-Sterilizing and Self-Cleaning of Silicone Catheters Coated with TiO2 Photocatalyst Thin Films: A Preclinical Work," J. Biomed. Mater. Res. 58:97-101.

Oliver et al. (2006), "An Impedimetric Sensor for Monitoring the Growth of *Staphylococcus epidermis*," Proc. 28th IEEE EMBS Annual Int'l Conf, Aug. 30-Sep. 8, 2006.

Ryder (Aug. 18, 2005), "Catheter-Related Infections: It's All About Biofilm," Topics in Advanced Practice Nursing eJournal 5(3).

Sekiguchi et al. (2007), "Self-Sterilizing Catheters with Titanium Dioxide Photocatalyst Thin Films for Clean Intermittent Catheterization: Basis and Study of Clinical Use," Int. J. Urology 14:426-430.

Yao et al. (2007), "Self-Sterilization Using Silicone Catheters Coated With Ag and TiO2 Nanocomposite Thin Film," J. Biomed. Mater. Res., Part B: Applied Biomaterials, pp. 453-460.

Liu et al. Mechanisms of the bactericidal activity of low amperage electric current (DC),J Antimicrobial Chemotherapy (1997) 39, 687-695.

International Search Report and Written Opinion in PCT/US2012/043403.

International Search Report and Written Opinion in PCT/US2012/043409.

PHOTOCATALYTIC DISINFECTION OF IMPLANTED CATHETERS

CROSS-REFERENCE TO RELATED APPLICATIONS

This application claims priority under 35 U.S.C. §119(e)(1) to provisional U.S. Patent Application Ser. No. 61/499,056, filed Jun. 20, 2011, the disclosure of which is incorporated by reference herein.

This invention was made with Government support under grant number 1P50FD003782-01 awarded by the Food and Drug Administration. The Government has certain rights in this invention.

TECHNICAL FIELD

The invention relates generally to implantable, "indwelling" catheters. More particularly, the invention relates to systems and methods for killing microorganisms in a biofilm on a catheter surface without removal of the catheter from a patient's body.

BACKGROUND

Microbial biofilms are formed when microorganisms adhere to a biotic or abiotic surface and produce extracellular macromolecules that facilitate adhesion to the surface and form a structural matrix that supports and protects the microorganisms. A biofilm is thus an accumulation of microorganisms such as bacteria embedded in an extracellular hydrated matrix primarily composed of exopolymers and other filamentous macromolecules, typically glycopeptides. Accordingly, a biofilm is generally described as a layer of bacteria (or other microorganisms), or as a plurality of layers and/or regions on a surface wherein bacteria are encased in a matrix of extracellular polymeric substances, or "EPS." A substantial fraction of the biofilm is actually composed of this matrix; see, e.g., Donlan (2001) *Emerging Infectious Diseases* 7(2): 277-281. Microorganisms in biofilms in many cases exhibit characteristics that are different from those seen with planktonic (freely suspended) microorganisms, particularly with respect to phenotypic traits like growth rate and resistance to antimicrobial treatment. It has been established that bacteria within biofilms can have up to a 1000-fold greater resistance to antibiotic agents than those grown under planktonic conditions, making eradication of a biofilm extremely difficult; see, e.g., Ceri et al. (1999) *J. Clin. Microbiol.* 37(6):1771-1776). One reason for this is the relative impenetrability of the biofilm—which can be both dense and thick—to antimicrobial agents. Another reason can be that the phenotype of sub-populations of cells in the biofilm changes so that the cells can better survive in the presence of antimicrobial agents; see Haagensen et al. (2007) *J. Bacteriol.* 189:28-37, and Folkesson and Haagensen et al. (2008) PLOSone, 3:e1891. Stability and resistance to dissolution are also key features of microbial biofilms; see Saville et al. (2011) *J. Bacteria* 193(13): 3257-64. An additional cause of antibiotic resistance may be that upregulation of efflux pumps can render biofilm cells able to transport unwanted antimicrobial agents out of cells in the biofilm; see Costa et al. (Oct. 27, 2011) *BMC Microbiol.* 11:241 and Nikaido et al. (2012) *FEMS Microbiol. Rev.* 36(2):340-63.

While biofilms can and do form on a variety of surfaces in a virtually unlimited number of contexts, biofilm formation in the medical arena is particularly concerning. As noted above, biofilm-related infections are extraordinarily tolerant to treatment with antimicrobial agents, and biofilm formation on medical implants is therefore extremely problematic. Microorganisms can attach to and develop biofilms on any type of medical implant, whether temporarily or permanently inserted or implanted in a patient's body, and can be a source of chronic bacterial infections. Chronic infections that are caused by biofilms on a medical implant (e.g., otitis media and osteomyelitis) often result in treatment failure and reoccurrence shortly after treatment. In 2005, biofilms accounted for about 65% of infections treated in the developed world. See Costerton et al. (1999) *Science* 284:1318-1322.

Medical devices are critical in modern-day medical practice. At the same time, they are major contributors to morbidity and mortality. The use of a medical device, particularly an implanted medical device or medical "implant," is the greatest exogenous predictor of healthcare-associated infection; Manangan et al. (2002) *Emerg. Infect. Dis.* 8:233-236. Most infections that arise in the hospital setting, or "nosocomial" infections, occur primarily at four sites within the body: the urinary tract; the respiratory tract; the bloodstream; and surgical wound sites. According to Ryder et al. (2005) *Topics in Advanced Practice Nursing eJournal* 5(3), the following chronic diseases occurring in the nosocomial context have been established as caused by or at least associated with biofilms: cystic fibrosis; endocarditis; otitis media; prostatitis; osteomyelitis; chronic wounds; myeloidosis; tonsillitis; periodontitis; dental caries; necrotizing fasciitis; biliary tract infection; and Legionnaire's disease.

It has been found that 95% of nosocomial urinary tract infections are caused by an infected urinary catheter, 86% of nosocomial pneumonias are caused by an infected mechanical ventilator, and 87% of nosocomial bloodstream infections are associated with an infected intravascular device. See Ryder et al., supra, citing Richards et al. (1999) *Crit. Care Med.* 27:887-892. As will be explained infra, nosocomial bloodstream infections associated with an implanted catheter are the most life threatening of the aforementioned nosocomial infections and associated with the most significant medical costs.

The medical implants must be removed in order to remove the biofilm and then re-inserted into a patient's body. Examples of implantable medical devices on which biofilms may form include, without limitation:

Catheters, e.g., arterial catheters, central venous catheters, dialysis tubing, endotracheal tubes, enteral feeding tubes, gastrostomy tubes, hemodialysis catheters, nasogastric tubes, nephrostomy tubing, pulmonary artery catheters, tracheotomy tubes, umbilical catheters, and urinary catheters;

Implants, e.g., arteriovenous shunts, breast implants, cardiac and other monitors, cochlear implants, defibrillators, dental implants, maxillofacial implants, middle ear implants, neurostimulators, orthopedic devices, pacemaker and leads, penile implants, prosthetic devices, replacement joints, spinal implants, and voice prostheses; and Other implanted devices such as artificial hearts, contact lenses, fracture fixation devices, infusion pumps, insulin pumps, intracranial pressure devices, intraocular lenses, intrauterine devices, joint prostheses, mechanical heart valves, ommaya reservoirs, suture materials, urinary stents, vascular assist devices, vascular grafts, vascular shunts, and vascular stents.

As indicated above, catheters are of particular interest because they are used in a host of medical applications and often involve critically ill and/or very young patients. Catheters are used not only in the administration of fluids and medication, but also in drainage of body fluids such as urine or abdominal fluids; angioplasty, angiography, and catheter ablation; administration of gases such as oxygen and volatile anesthetic agents; and hemodialysis. A central venous catheter (also referred to as a "central line" or "CVC") is a widely used catheter that is placed in a large vein in the neck, chest, or groin and serves as a conduit for delivering medications, parenteral nutrition, and fluids. A CVC is commonly used in plasmapheresis, dialysis, and chemotherapy, and is also relied upon for obtaining to obtain critically important measurements, such as central venous pressure ("CVP").

Catheter-associated bloodstream infections (CABSIs; also referred to as catheter-related bloodstream infections, or CRBSIs) are a leading cause of morbidity and mortality in hospital settings. Each year 250,000 documented CABSIs occur in the United States, with an attributable mortality in the range of about 12% to 25% and an estimated cost to treat of $25,000 per episode ($6.2 billion annually, as of 2002). The intensive care environment accounts for 80,000 of these infections, with an attributable mortality as high as 35% and a cost to treat at $56,000 per episode. See Department of Health & Human Services, USA: Guidelines for the Prevention of Intravascular Catheter-Related Infections, 2011. Diagnosis is difficult and clinical suspicion of infection frequently leads to removal and replacement of indwelling catheters, resulting in significant healthcare costs and requiring that patients be subjected to additional procedures. The approaches that have been taken to counteract the widespread problem have not succeeded in either preventing biofilm formation or eliminating a biofilm that has formed without removal of the catheter from a patient's body.

While biofilm formation is generally problematic with implantable medical devices, it will be appreciated that the risk of infection is that much higher with catheters such as the CVC that remain in place for an extended time period. The most common bacteria found in CVC biofilms are *Staphylococcus aureas, Staphylococcus epidermis sepsis, Candida alb cans, Pseudomonas aeruginosa, Klebsiella pneumoniae,* and *Enterococcus faecalis*. These bacteria may originate from patient's skin microflora, exogenous microflora from health care personnel, or contaminated infusions, and can migrate from the skin along the exterior surface or internally from the catheter hub or port.

It has been found that biofilm formation on CVCs is universal and that virtually all in-dwelling CVCs are colonized by microorganisms in a biofilm. Biofilms form not only on the outer surface of the catheter, but also on the inner lumen of the catheter, particularly with long-term catheterization; see Raad et al. (1998) *Lancet* 351:893-98.

The most prevalent approach to preventing CABSIs—hand washing and the use of aseptic techniques when handling the catheter—can be unreliable even in the highly controlled setting of a hospital. Other techniques such as ethanol lock therapy, or "ELT," may degrade catheter materials and are not effective with respect to biofilms that are downstream from the inlet point. Catheters have been made with antibacterial coatings, including minocycline, chlorhexidine, and silver (see Aslam (2008), "Effect of Antibacterials on Biofilms," Section of Infectious Diseases, Assoc. *Prof Infect. Control Epidemiol.* 5175:e9-e11), but the antibacterial efficacy of all of these coated catheters, wanes over time due to coating degradation; moreover, the coating method is not effective against nonbacterial organisms such as fungus, the coatings may selectively target only a particular type of bacteria, they can promote antibiotic resistance, and they are significantly more expensive than typical catheters. (Aslam, supra; Donlan, supra).

In the hospital setting, patients with indwelling catheters who have febrile illness and elevated inflammatory markers are suspected of having a CABSI. Blood cultures drawn from peripheral sites in these patients are compared with those drawn from the suspected catheter. If catheter cultures are positive, a line infection is suspected, particularly if peripheral cultures are negative. This method for verifying catheter infection is highly inaccurate, however, having a high false-positive rate because bacteremia from other sources can also result in a positive test result. Thus, a catheter may be identified as infected when it actually is not. Currently, there is no highly specific, sensitive method for detecting catheter infection. Once a catheter is suspected of infection, first-line therapy is typically treatment with antibiotics. However, biofilm formation renders such therapy ineffective, as noted earlier, and antimicrobial agents can single out resistant organisms. In many cases, surgical removal of the catheter is necessary, resulting in increased healthcare costs, additional and sometimes unnecessary surgical procedures for patients, and reduction in potential venous access sites in patients who may be line-dependent for nutrition and pharmacotherapy.

Oxidizing agents are sometimes used to remove biofilms from catheters and other structures and devices, but have not been employed on implants inside the body. While bleach, ozone, and hydrogen peroxide are common oxidizing agents for eliminating biofilms, and oxidation is the most effective treatment for destroying biofilms, the limitation of such common agents is in the mode of application. They must diffuse through the biofilm, from the outside, as dead cells on the biofilm surface protect the inner layer. For an in vivo catheter, this approach is unworkable, because high concentrations of oxidizing agents cannot be safely added to the blood and limited to a local region within the body.

For instance, Ohko et al. (2001) *J. Biomed. Mater. Res.* 58:97-101 and Sekiguchi et al. (2007) *Int. J. Urology* 14:426-430 describe the implementation of titanium dioxide photocatalysis to produce a bactericidal effect on surfaces. Titanium dioxide ($TiO_2$), or "titania," is known to be a chemically stable and biocompatible material that upon illumination with ultraviolet light can degrade organic compounds by generating hydroxyl radicals (.OH) and superoxide anion ($O_2^-$). The Sekiguchi et al. clinical evaluation necessarily involved removal of the titanium dioxide-coated catheters for UV sterilization, while Ohko et al. similarly note that the part of the titania coating that is contained within a patient's body "cannot" be illuminated. Ohko et al. additionally pointed to the difficulty of coating silicone materials, such as silicone catheters, with titania photocatalyst because of the poor wettability of the silicone surface by the coating solution (pages 97-98, bridging paragraph). The solution Ohko et al. came up with was to pre-treat the catheter surface with sulfuric acid to sulfonate the polymer surface and thus roughen it without causing damage. To date, however, there has been no development of a photocatalytic system for catheter disinfection and biofilm elimination that can be employed without removal of the catheter from a patient's body.

The problem of infection is not limited to venous catheters, but also affects other types of catheters and medical devices as indicated above, such as urinary catheters, ventriculoperitoneal shunts, in-dwelling catheter-like prostheses (vascular conduits), dialysis tubing, endrotracheal tubes, Foley catheters, and the like. Based on these considerations, a long-felt need is apparent for technology that can safely and effectively destroy a biofilm, i.e., kill microorganisms in the biofilm. Such a system would have widespread application in medicine, resulting in tremendous savings in healthcare costs, reduced morbidity and mortality, and assist in preventing further antibiotic resistance. It would also be optimal to provide a system that could not only kill microorganisms within a biofilm but also prevent biofilm formation. Ideally, such a system would also be portable and easily controlled by a patient outside of a hospital setting. It would in addition be beneficial to be able to implement a system that meets the aforementioned requirements in the detection of a biofilm that has formed or is in the process of forming. Such a catheter would significantly reduce the risk of infection, decrease the frequency with which patients need to be re-catheterized, sense infections before symptoms become apparent so that preventive measures can be taken, and because infection would be treated at the source by killing bacteria on the catheter surfaces, would lead to less need for general antibiotics.

SUMMARY OF THE INVENTION

Accordingly, it is a primary object of the invention to address the aforementioned need in the art by providing a method and system for inhibiting a biofilm on the surface of an implanted catheter, i.e., for killing microorganisms in a biofilm that is present or forming on the catheter surface, and/or preventing biofilm growth. The invention involves the creation of powerful oxidizing agents in the localized region of the catheter surface, which are destructive to biofilms and prevent biofilm growth. As noted above, however, effective concentrations of oxidizing agents cannot be safely added to the blood and limited to a local region within the body. The present invention, by contrast, makes use of a system and process that generate oxidizing agents at the catheter surface, in the immediate vicinity of the biofilm; the oxidizing agents include Reactive Oxygen Species ("ROS") such as the hydroxyl radical (HO.) and the superoxide anion ($O_2^-$), as well as further oxidizing species generated upon their decay and interaction with other molecules. The hydroxyl radical and the superoxide anion are powerful oxidizers, but exist in the body for only a short time, the hydroxyl radical because of its reactivity and the superoxide anion largely because of the activity of the superoxide scavenging enzyme SOD. The invention circumvents the problem by implementing a system and method for generating these oxidizing agents at the catheter surface, and does so without requiring removal of the implanted catheter from a patient's body and without need for added biocidal agents.

In one aspect of the invention, an implantable catheter is provided that can be photocatalytically disinfected without removal of the implanted catheter from the body of a patient. The implantable catheter comprises: an elongate catheter body of predetermined length having a proximal end, a distal end, at least one lumen extending through the catheter body and adapted to transport fluid from the proximal end to the distal end, an outer surface on the exterior of the catheter body, and an inner surface on the interior of the lumen; an outer photocatalytic layer on the outer surface that undergoes a photocatalysis reaction upon irradiation with ultraviolet light to generate ROS; an out-coupling means for facilitating out-coupling of ultraviolet light directed into the catheter at the proximal end so that along the length of the catheter a first portion of the light is refracted toward the catheter surfaces and thus toward the outer photocatalytic layer, thereby activating the photocatalysis reaction; and an out-coupling regulating means for ensuring that the amount of out-coupled ultraviolet light is substantially uniform along the length of the catheter from the proximal end to the distal end. The substantial uniformity of the outwardly directed light along the length of the catheter generates an approximately constant concentration of ROS in the localized region of the catheter surface, in the vicinity of a growing or existent biofilm, along the length of the catheter.

In another aspect of the invention, an implantable catheter is provided as above in which the photocatalytic layer is composed of crystalline titanium dioxide, generally containing at least 50% anatase titania.

In another aspect of the invention, the catheter body of the implantable catheter is composed of a material that is substantially transparent to ultraviolet light, i.e., to ultraviolet light of the wavelength that will be used in irradiating the catheter body. In this embodiment, ultraviolet light can be directed into the catheter walls so that the catheter body serves as the light guide for illuminating and activating the photocatalytic layer, eliminating the need for introduction of a separate light guide, e.g., a fiber optic, into the lumen of the catheter. In this embodiment, the implantable catheter generally has a fiber optic means built in to the catheter body that extends longitudinally along the length of the catheter, which, as noted above, enables irradiation through the catheter body itself rather than through an inserted or built-in lightguide. In other embodiments, the implantable catheter includes an additional means for carrying light through the catheter from the proximal end to the distal end, as will be discussed in detail infra.

By "substantially transparent" is meant that the material employed for the catheter body transmits greater than about 80% of the ultraviolet light at the wavelength used. Since absorbance A is by definition equal to $2-\log_{10}\%$ T, where "% T" indicates the percent of light transmitted, this means that the corresponding absorbance is less than about 0.1.

In another aspect of the invention, the radial emergence of light is controlled along the length of the catheter by the incorporation of scattering particles in the catheter body as the out-coupling means, i.e., as the means for facilitating out-coupling of the light pumped in to the catheter. In a related aspect of the invention, the out-coupling means encompasses an internal, tubular reinforcing element that is substantially transparent to ultraviolet light of the wavelength used, e.g., a braid or weave. In other related aspects, surface texturing, embedded surface particles, and incorporation of bubbles in the catheter body additionally or alternatively serve to facilitate out-coupling.

In an additional aspect of the invention, the implantable catheter includes a means for ensuring that the amount of out-coupled light is substantially uniform along the length of the catheter, i.e., an out-coupling regulating means, which encompasses the incorporation of the out-coupling means at a density gradient that increases axially along the length of the catheter from the proximal end to the distal end.

In another aspect of the invention, an implantable catheter is provided that can be photocatalytically disinfected without removal from a patient's body, comprising an elongate catheter body of predetermined length having a proximal end, a distal end, at least one lumen extending through the catheter body and adapted to transport fluid from the proximal end to the distal end, an outer surface on the exterior of the catheter body, and an inner surface on the interior of the lumen; an inner photocatalytic layer on the inner surface that undergoes a photocatalysis reaction upon irradiation with ultraviolet light to generate reactive oxygen species; an out-coupling means for facilitating out-coupling of ultraviolet light directed into the catheter at the proximal end so that along the length of the catheter a first fraction of the light is refracted toward the catheter surfaces and thus toward the inner photocatalytic layer, thereby activating the photocatalysis reaction; and an out-coupling regulating means for ensuring that the amount of out-coupled ultraviolet light is substantially uniform along the length of the catheter from the proximal end to the distal end.

In another aspect of the invention, the implantable catheter additionally includes a light confinement means to enable illumination of the catheter body along the entire length thereof, by causing a second portion of the light pumped in to be internally reflected and thus able to travel axially down the length of the catheter to the distal end. The light confinement means, in one embodiment, includes a cladding layer that has a lower index of refraction than the catheter body. In this embodiment, the light confinement means serves as the outer surface of the catheter, i.e., is interposed between the catheter body and the photocatalytic layer, such that the photocatalytic material is embedded in or present as a layer on the cladding layer.

In still another aspect of the invention, the implantable catheter includes a structural reinforcing means for increasing the tear strength of the catheter. The structural reinforcing means may or may not double as the out-coupling means.

In a further aspect of the invention the implantable catheter additionally includes a photocatalytic layer on the inner surface of the lumen, which may or may not be composed of the same photocatalytic material as the photocatalytic layer on the outer surface of the catheter body.

In still a further aspect of the invention, the implantable catheter includes a means for imparting radio opacity to the catheter body to enable visualization of the implanted catheter using medical imaging technology, e.g., X-ray, MRI, CT technology, fluoroscopy, or the like.

In yet another aspect of the invention, the implantable catheter is provided with a sensor that can detect or confirm the presence or formation of a biofilm on at least the outer surface of the catheter. In this embodiment, the implantable catheter is provided with a means for quantifying a parameter that corresponds to the increasing presence of microbes on the catheter surface.

In another aspect of the invention, an implantable catheter system is provided that includes the implantable catheter and an ultraviolet ("UV") light source, and a power source operably connected to and capable of powering the light source, where the light source will generally be a source of UVA, i.e., light having a wavelength in the range of about 320 nm to about 387 nm, a wavelength range that is optimal for many photocatalysts, including titanium dioxide.

In a related aspect of the invention, the light source enables portability of the implantable catheter system. For instance, the light source may be a simple LED, which can be powered by a small battery that may be carried or worn by the patient or implanted with the system. In another aspect, the light source is a UV laser or mercury lamp. The latter two light sources can operate at significantly higher power, on the order of 50 mW to about 200 mW, while total power to the UV LED is, by contrast, on the order of 10 mW. In still another related aspect of the invention, the power source is wirelessly connected to the light source and capable of powering the light source remotely, as may be enabled by incorporating an inductive powering means in the power source, with the light source provided with a corresponding antenna.

In a further aspect, the invention provides a method for inhibiting a biofilm surface of the implantable catheter described above, where biofilm "inhibition" encompasses killing microorganisms in a biofilm growing or present on the surface of the catheter and/or preventing biofilm growth, as noted above. The method comprises irradiating the implantable catheter without removal of the catheter from the patient's body, by directing ultraviolet light into the catheter at the proximal end so as to activate the photocatalysis reaction on at least the outer surface of the catheter along the length thereof. By directing ultraviolet light "into the catheter" or "into the catheter body," and similarly by "irradiating the catheter" or "irradiating the catheter body," applicants intend to encompass irradiation of the catheter wall, irradiation of the lumen, or both.

In another aspect, the invention additionally includes a method for detecting or confirming the presence or formation of a biofilm on at least the outer surface of the catheter prior to irradiation of the catheter and consequent activation of the photocatalytic layer.

Additional aspects, features, and objects of the invention will become more fully apparent when the Detailed Description below is read in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Definitions and Nomenclature:

Unless defined otherwise, all technical and scientific terms used herein have the meaning commonly understood by one of ordinary skill in the art to which the invention pertains. Specific terminology of particular importance to the description of the present invention is defined below.

In this specification and the appended claims, the singular forms "a," "an" and "the" include plural referents unless the context clearly dictates otherwise.

The term "implantable catheter" as used herein refers to a catheter that is implanted or inserted in the human body either temporarily or permanently.

The term "inhibition" as applied to the capability of the invention to inhibit biofilm growth refers to the process of killing microorganisms in a biofilm that is present or forming on a surface, and thus includes all of the following: elimination or destruction of a biofilm; disruption of a biofilm; reduction in the thickness of a biofilm; the killing of some or all of the microorganisms within a biofilm; and prevention of biofilm growth.

The term "disinfection" as used herein refers to biofilm inhibition as defined above, typically referring to the killing of microorganisms within a biofilm on a catheter surface.

The term "biofilm" refers to a matrix-enclosed microbial accretion on and anchored to the surface of an implanted medical device.

The term "biofilm formation" is intended to include the formation, growth, and modification of the bacterial or other colonies contained with biofilm structures, as well as the synthesis and maintenance of the polysaccharide matrix of the biofilm structures.

By a "braid" is meant a structure in which three or more elongated elements (e.g., wires or threads) or intertwined, wherein the elements are interfaced diagonally to the production axis of the material.

By a "weave" is meant a woven medical structure in which two elongated elements (e.g., wires or threads) are interlaced so that they cross each other at right angles to one another; the warp elements run lengthwise and the filling threads, or "weft elements" run transverse to the warp elements.

The Implantable Catheter:

The implantable catheter of the invention is thus one that can be photocatalytically activated to kill infecting microorganisms in a biofilm present on its exterior and/or interior surfaces and/or prevent biofilm growth thereon. The infecting microorganisms in the biofilm are typically bacterial cells, but there may also be colonies of yeast, fungi, mold, or other colonizing microorganisms in the biofilm.

Figure 1:
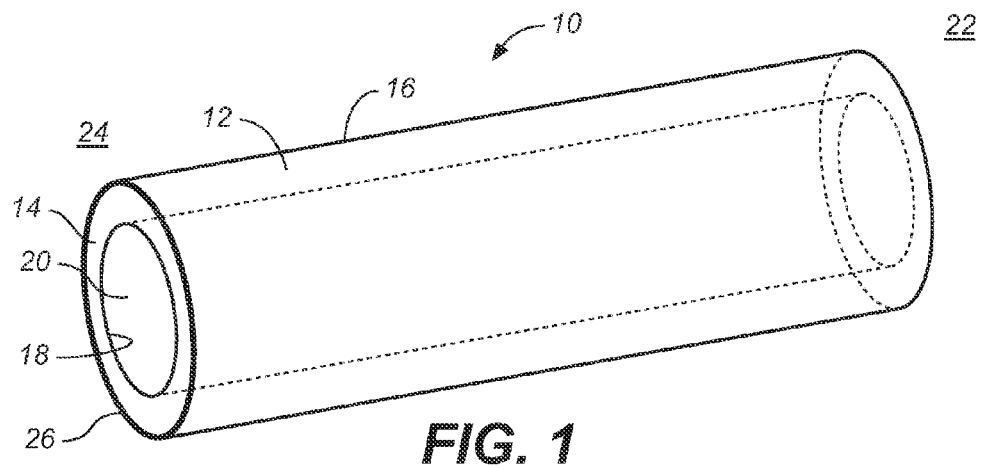
FIG. 1 illustrates in perspective, partially cut-away view a representative segment of an implantable catheter of the invention with a photocatalytic layer on the outer surface of the catheter.

FIG. 1 illustrates a representative segment of one such catheter, shown generally at 10. As may be seen in the figure, the catheter is composed of an elongate catheter body 12 having a continuous, substantially cylindrical annular wall 14 defining an outer catheter surface 16 and an inner catheter surface 18. The wall 14 of catheter body 12 also defines a central hollow lumen or passageway 20, through which fluid can flow from proximal region 22 to distal region 24 in connection with any of a variety of diverse medical applications. Proximal region 22 terminates in an inflow tip at the proximal end of the catheter, while distal region 24 terminates in an outflow tip at the distal end of the catheter. An outer photocatalytic layer 26 surrounds the outer catheter surface 16, and is composed of a material that undergoes a photocatalysis reaction upon irradiation with ultraviolet light, to generate ROS such as the hydroxyl radical (HO.) and the superoxide anion ($O_2^-$), as well as further oxidizing species generated upon their decay and interaction with other molecules. The implantable catheter also includes an out-coupling means for facilitating out-coupling of ultraviolet light directed into the catheter at the proximal end, so that along the length of the catheter a first fraction of the light pumped in is refracted outwardly, e.g., radially, toward the catheter surfaces and thus toward the photocatalytic layer, thereby activating the photocatalysis reaction. Also in included is an out-coupling regulating means for ensuring that the amount of out-coupled ultraviolet light, i.e., that the first fraction of the light that is refracted outwardly, is substantially uniform along the length of the catheter from the proximal end to the distal end. The out-coupling means and the out-coupling regulating means (not shown in FIG. 1) will be described in further detail infra.

Figure 2:
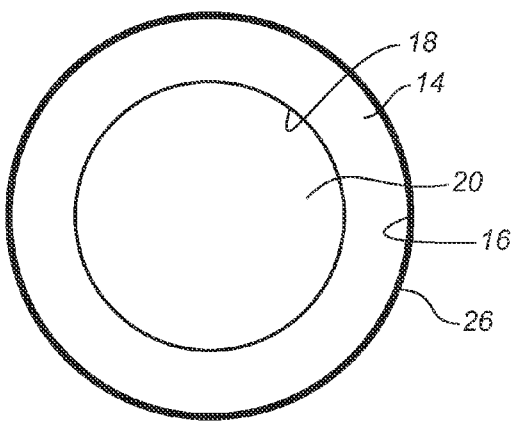
FIG. 2 is a cross-sectional view of the catheter segment of FIG. 1.

FIG. 2 illustrates the segment of FIG. 1 in cross-sectional form, with outer catalytic layer 26 shown disposed on outer catheter surface 16, with an uncoated inner catheter surface 18.

In the implantable catheter represented in FIG. 1 and FIG. 2, and in all of the embodiments described and shown herein, the photocatalytic layer can be composed of any suitable compound, composition, or material that is biocompatible, inert with respect to the other components of the catheter and catheter system, and capable of generating ROS upon irradiation with ultraviolet light. Exemplary materials include titanium dioxide, zinc oxide, and alumina. A preferred photocatalytic material is composed of titanium dioxide, particularly crystalline titanium dioxide, as amorphous titanium dioxide has low photocatalytic activity. Crystalline titanium dioxide can exist in one of three forms or phases, each with a different crystalline structure: anatase; rutile; and brookite. Anatase and brookite titania tend to be more photocatalytically active, and are generally preferred herein, as are combinations thereof; however, it should be noted that it has also been reported that anatase-rutile combinations exhibit a higher level of photocatalytic activity relative to either the anatase form or the rutile form alone. In a particularly preferred embodiment herein, the titanium dioxide employed is in the form of crystalline particles composed of at least 50% anatase titania, with the remainder in the brookite and/or rutile forms. Crystalline titania may be obtained commercially (e.g., as Aeroxide® $TiO_2$ P-25 from Evonik Industries, Essen, Germany) or synthesized using methods known to those of ordinary skill in the art and/or described in the pertinent texts and literature. See, e.g., Reyes-Coronado et al. *Nanotechnology* 29:145605 (doi:10.1088/0957-4484/19/14/145605), which describes a recently developed technique for synthesizing anatase, rutile, and brookite titanium dioxide nanoparticles from amorphous titania, and de Farias (November/December 2002) *Quim Nova* 25(6) (São Paolo), which describes a sol-gel process for synthesizing anatase phase titania powder from titanium tetrabutoxide. The particle size of the titania used will typically be in the range of about 10 nm to about 300 nm, e.g., in the range of about 100 nm to about 300 nm, or in the range of about 20 nm to about 200 nm. Larger particle sizes within the latter range may be preferred, insofar as particles closer to 20 nm have been found to aggregate in air and water, while particles on the order of 200 nm were not; see Gurr et al. (2005) *Toxicology* 213:66-73.

In addition, in the implantable catheter represented in FIG. 1 and FIG. 2 as well as in all of the embodiments described and shown herein, the catheter body is manufactured from a flexible elastomeric material that is biocompatible and inert under the conditions of use, with respect to, for example, body fluids and tissue, the reactive biocidal species, and ultraviolet light. In addition, the material should also provide the catheter with sufficient flexibility to allow the catheter body to bend, twist, and undergo some degree of deformation. Accordingly, the catheter body is preferably made of a strong yet flexible polymeric material, such as a crosslinkable polysiloxane (silicone), e.g., poly(dimethylsiloxane) (PDMS), a fluoropolymer, poly(vinyl chloride) (PVC), and amorphous versions of aliphatic polymers such as polyethylene or polypropylene.

The catheter material should also be substantially transparent to ultraviolet radiation. By "substantially transparent" is meant that the material employed for the catheter body transmits greater than about 80% of the ultraviolet light at the wavelength used, e.g., a wavelength in the range of about 320 nm to about 387 nm. Since, as noted earlier herein, the absorbance A is equal to $2-\log_{10}\%$ T, the corresponding absorbance will be less than about 0.1. Preferably, the catheter material transmits greater than about 90% of the ultraviolet light used, which corresponds to an absorbance A of less than about 0.05. A less transparent catheter body would interfere with the efficiency of the system and reduce the amount of out-coupled light as well as the amount of light reaching the distal region of the catheter. A preferred material for the catheter body is a silicone polymer that is substantially free of unsaturated bonds, as unsaturated bonds are UV-absorbent. Commercially available silicones usually have some double bond contamination, resulting from side chain substituents such as ethyl vinyl groups and propyl vinyl groups), and it is important in the present context to avoid use of such materials. The silicone that is useful herein may be synthesized in a manner that does not result in unsaturated side-chains or may be prepared by hydrogenation of commercially available silicone containing unsaturated bonds in the presence of hydrogen or a hydrogen-containing gas such as forming gas (40% $H_2$ in $N_2$) at elevated temperature in the presence of a suitable hydrogenation catalyst. Biocompatibility of the silicone used as the catheter body may be ensured by eliminating potentially toxic contaminants, avoiding synthetic processes that yield potentially toxic-by-products, and/or by using a silicone material supplied as acceptable for short-term or long-term implantation in the human body (e.g., those silicones available from NuSil Technology LLC (Carpinteria, Calif.)).

In a preferred embodiment, illumination of the catheter body to activate the photocatalytic reaction on the catheter surface is done using the catheter itself as a lightguide, insofar as the catheter body is substantially transparent to ultraviolet light of the wavelength used in photocatalytic activation. In this way, ultraviolet light can be directed into the catheter walls so that the catheter body serves as the light guide for illuminating and activating the photocatalytic layer, eliminating the need for introduction of a separate light guide, e.g., a fiber optic, into the lumen of the catheter. In this embodiment, the implantable catheter generally has a fiber optic means built in to the catheter body that extends longitudinally along the length of the catheter, which, as noted above, enables irradiation through the catheter body itself rather than through an inserted or built-in lightguide. In other embodiments, other ways of carrying light through the catheter body can be implemented.

For instance, flexible, substantially UV-transparent fused silica rods can be embedded in the catheter body and extend along the length of the catheter from the proximal end to the distal end. As another example, an additional light carrying means may be in the form of an aqueous liquid contained in one or more channels in the catheter body, extending along the length of the catheter from the proximal end to the distal end.

Figure 3:
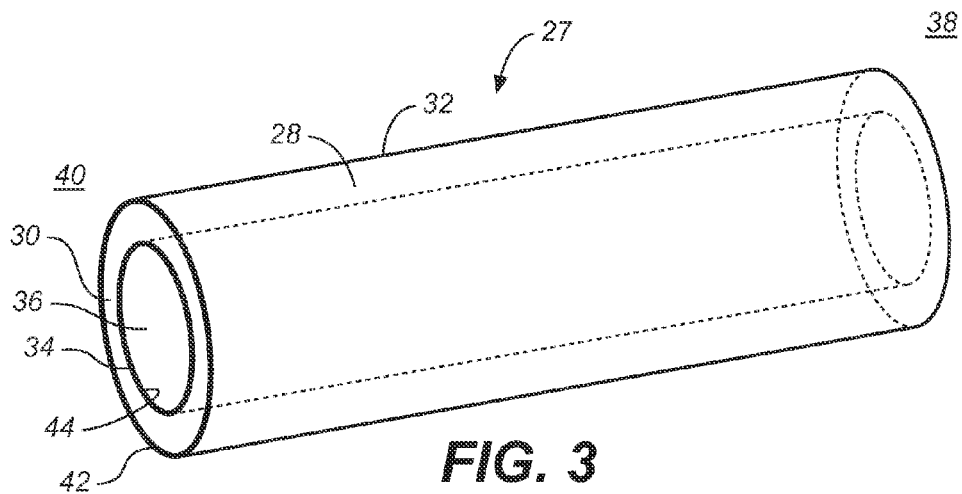
FIG. 3 illustrates in perspective, partially cut-away view a representative segment of an implantable catheter of the invention with a photocatalytic layer on both the inner and outer surfaces of the catheter.

FIG. 3 illustrates another embodiment of a representative segment of an implantable catheter of the invention, which, as may seen in the figure, has both an inner photocatalytic layer and an outer photocatalytic layer, enabling photocatalysis activation on both the inner and outer catheter surfaces. As in the representative segment of FIG. 1, the catheter 27 of FIG. 3 is composed of an elongate catheter body 28 having a continuous, substantially cylindrical annular wall 30 defining an outer catheter surface 32 and an inner catheter surface 34. The wall 30 of catheter body 28 also defines a central hollow lumen or passageway 36, through which fluid can flow from proximal region 38 to distal region 40 in connection with any of a variety of diverse medical applications. An outer photocatalytic layer 42 is disposed on the outer catheter surface 32, and is composed of a material that undergoes a photocatalysis reaction upon irradiation with ultraviolet light, to generate ROS on the exterior of the catheter, while an inner photocatalytic layer 44 is provided on the inner surface 34, which similarly is composed of a material that photocatalytically generates ROS upon irradiation with ultraviolet light. The inner and outer photocatalytic layers may or may not be composed of the same photocatalytic material.

Figure 4A:
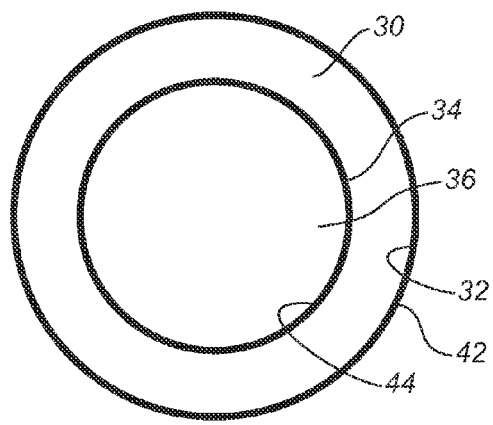
FIG. 4A is a cross-sectional view of the catheter segment of FIG. 3.

FIG. 4A illustrates the segment of FIG. 3 in cross-sectional form, with outer photocatalytic layer 42 shown disposed on outer catheter surface 32, and with inner photocatalytic layer 44 provided on the inner catheter surface 34.

Figure 4B:
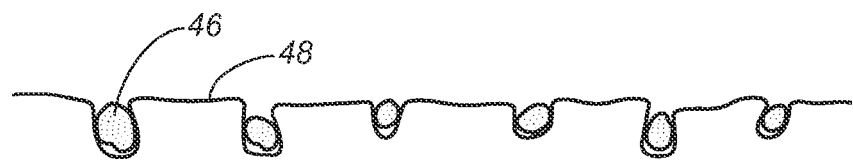
FIG. 4B is a representation of a catheter surface with embedded particles of photocatalytic material.

In the foregoing figures, the photocatalytic layer is illustrated as a coating on the exterior of the catheter, i.e., as a layer on the outer catheter surface. Typically, the photocatalytic layer has a thickness in the range of about 20 nm to 1 μm, preferably in the range of about 20 nm to about 200 nm, wherein a 20 nm layer of titanium dioxide is approximately a monolayer. The photocatalytic layer is not necessarily a coating, however; instead, the photocatalytic layer may be composed of particles of photocatalytic material that are embedded in or absorbed into the outer surface of the catheter and thus integral therewith. FIG. 4B illustrates one such embodiment, with particles 46 of photocatalytic material embedded in a surface 48, which may be an inner catheter surface or an exterior catheter surface, or, in some embodiments, in which a cladding or other light confinement means surrounds the catheter body, a surface of such an additional layer.

Figure 5:
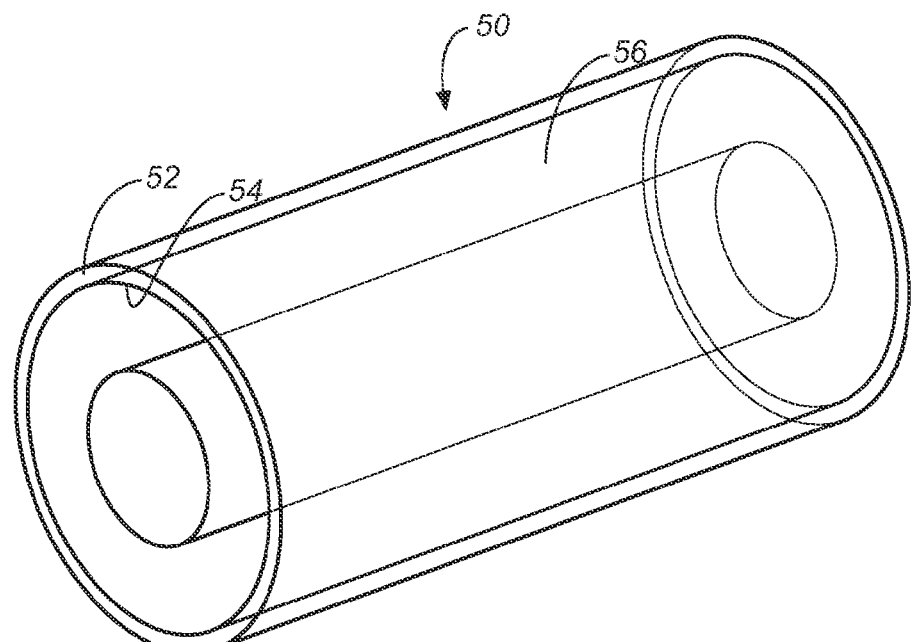
FIG. 5 is a perspective view of a representative segment of an implantable catheter of the invention with an outer cladding layer as a light confinement means.
Figure 6:
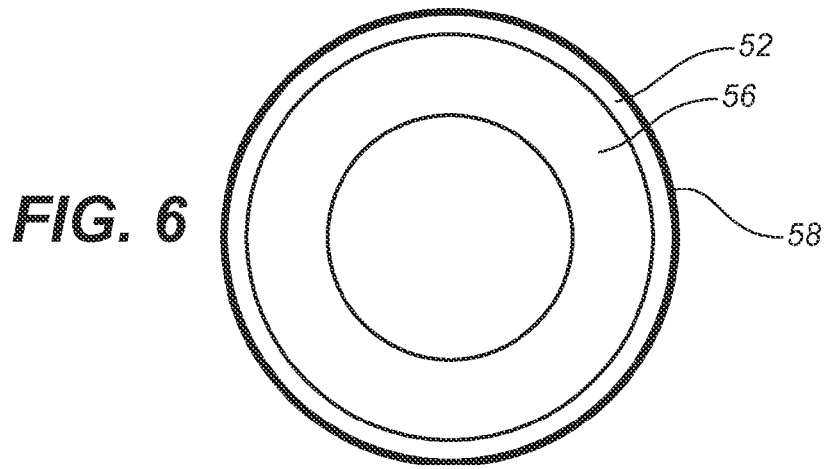
FIG. 6 is a cross-sectional view of an implantable catheter of the invention shown with a cladding layer as a light confinement means interposed between the catheter body and the photocatalytic layer.
Figure 7:
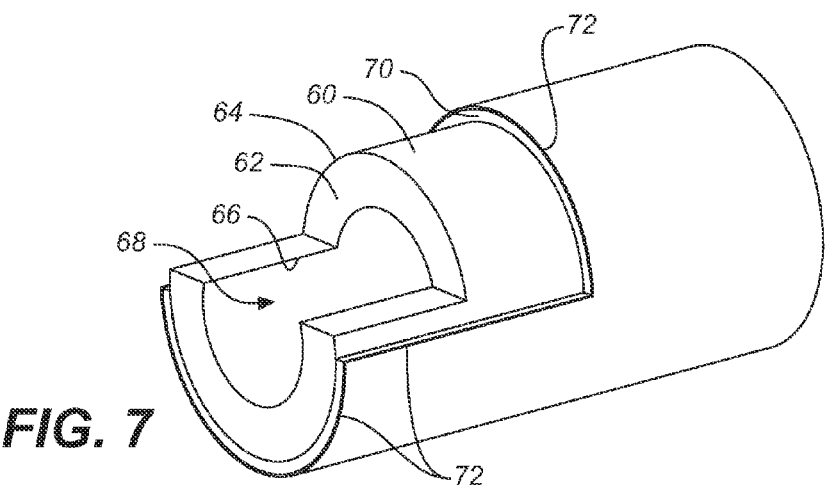
FIG. 7 is a perspective view of a catheter segment corresponding to the catheter of FIG. 7, in which the cladding layer and the catheter wall are shown partially cut-away to reveal the interior structure of the implantable catheter.

FIG. 5 illustrates an additional embodiment of the invention, wherein a catheter 50 analogous to that of either FIG. 1 or FIG. 2 is provided with an exterior light confinement means such as a cladding layer 52 disposed on the outer surface 54 of the catheter body 56. Inner surface 56 is uncoated. In this embodiment, the light confinement means serves as the outer surface of the catheter, i.e., is interposed between the catheter body and the photocatalytic layer, such that the photocatalytic material is embedded in or present as a layer on the cladding layer. In FIG. 6, the photocatalytic layer 58 is shown, representing the outermost element of the structure overlying cladding layer 52 and catheter body 56. FIG. 7, in which the cladding material and catheter wall are partially cut away to reveal the interior structure, the annular wall 62 of elongate catheter body 60 defining the outer catheter surface 64 and inner catheter surface 66, with the lumen shown at 68. Cladding layer 70 is shown surrounding the catheter and positioned overlying outer catheter surface 64. In this embodiment, the photocatalytic layer 72 is shown on the exterior surface of the catheter, on cladding 70. The material selected for the cladding layer must have a lower index of refraction than the catheter body, to ensure that a portion of the light pumped into the catheter body is internally reflected and able to travel axially along the entire length of the catheter to the distal end. Suitable materials for the cladding layer include, without limitation, fluoropolymers, PVC, and amorphous versions of aliphatic polymers such as polyethylene and polypropylene. Fluoropolymer cladding is preferred. Representative such materials include, by way of example rather than limitation, fluorinated ethylene propylene (FEP) resin and perfluoroalkoxy copolymer (PFA) resin. The thickness of the cladding layer is generally in the range of about 0.01 mm to about 0.5 mm, more typically in the range of about 0.03 mm to about 0.3 mm.

In general, the outer diameter ("OD"; the distance from outer surface to outer surface across cross-section of the catheter) will be in the range of about 1 mm to 2.5 mm, corresponding to a range of about 3 to 7.5 French ("Fr", where 1 Fr=3×OD in mm). The wall thickness is generally about 0.5 mm, while the catheter length can vary a great deal depending on the application, anywhere from several centimeters to several meters, averaging about 10 cm to 40 cm in most contexts.

A significant advantage of the invention is that the implantable catheter system is designed so that the amount of refracted, or out-coupled, light scattered toward the photocatalytic layer or layers is consistent along the length of the catheter, meaning that the concentration of ROS generated along the catheter surface(s) will have little if any variability, while ensuring that there is still a sufficient amount of light to reach the distal tip and activate the photocatalytic layer(s) so inhibit biofilm growth all the way to the distal tip. The outward emergence of light is controlled along the length of the catheter using an out-coupling means such as scattering particles. In the aforementioned embodiment, i.e., when scattering particles are used, they are selected so as to be of a material, size, and shape to effectively refract a sufficient amount of light to the exterior of the catheter and thus to the photocatalytic layer. The material selected for the scattering particles may be either organic, such as polystyrene spheres, or inorganic, such as fumed silica particles. It should be noted, however, and as will be appreciated by those of ordinary skill in the art, that the scattering particles must have an index of refraction sufficiently different from that of the catheter body in which they are dispersed in order to function effectively. In a preferred embodiment, the material selected for the scattering particles is substantially transparent to ultraviolet light of the wavelength used to illuminate the catheter. Generally, although not necessarily, a suitable size range for the particles is on the order of 0.5 μm to about 1.5 μm. The particles may also have any number of dimensions and shapes and is not limited in that regard; spheres, fibers, coils, and the like may all be advantageously employed.

Figure 8:
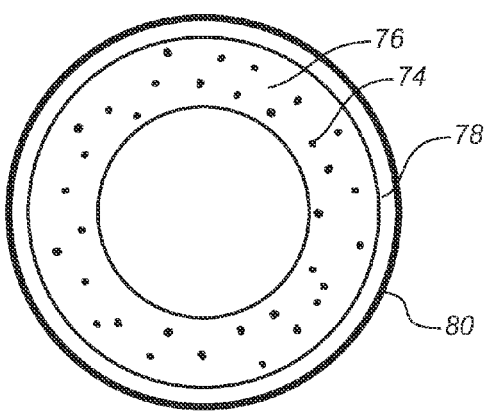
FIG. 8 is a cross-sectional view of an implantable catheter of the invention shown with a cladding layer as a light confinement means interposed between the catheter body and the photocatalytic layer, and scattering particles dispersed in the catheter body.
Figure 9:
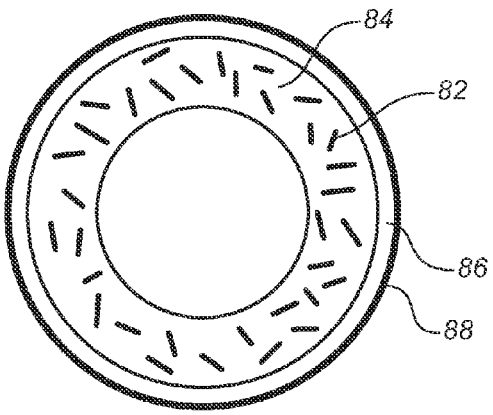
FIG. 9 is a cross-sectional view of an implantable catheter of the invention shown with a cladding layer as a light confinement means interposed between the catheter body and the photocatalytic layer, and scattering fibers dispersed in the catheter body.

In FIG. 8, scattering particles 74 are shown dispersed in the catheter body 76, approximately evenly distributed throughout the area of the cross-section shown. In the embodiment of FIG. 8, cladding layer 74 is shown overlying the catheter body and provided with a photocatalytic layer 76. FIG. 9 shows an analogous embodiment wherein the scattering particles are shown in the form of elongate fibers 82 dispersed within catheter body 84, with cladding layer 86 again shown overlying the catheter body and provided with a photocatalytic layer 88.

Figure 10:
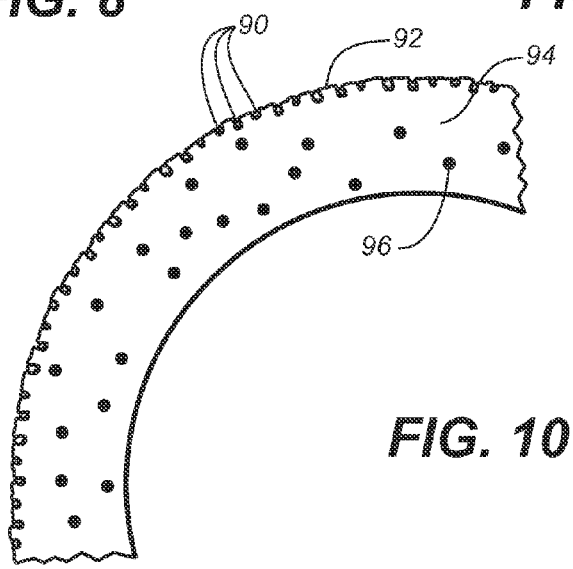
FIG. 10 shows a partial cross-section of an implantable catheter of the invention, showing photocatalytic particles embedded in the outer surface of the catheter body and scattering particles dispersed within the catheter wall.
Figure 11:
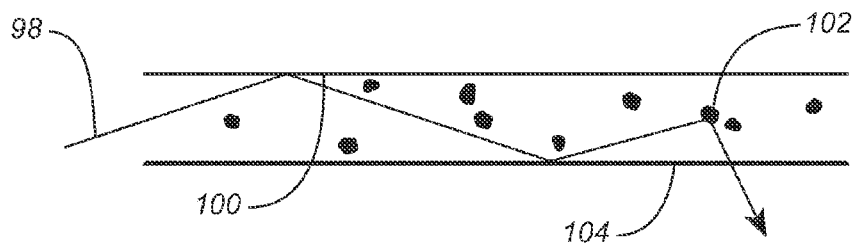
FIG. 11 schematically illustrates how the interior scattering particles function to refract light directed in to the catheter.

FIG. 10 shows a partial cross-section of an implantable catheter of the invention, showing photocatalytic particles 90 such as titanium dioxide particles embedded in the outer surface 92 of the catheter body 94, and scattering particles 96 again dispersed within the catheter wall. FIG. 11 illustrates how the scattering particles function to refract inwardly directed light 98, shown as initially reflecting off of the catheter surface 100, but then refracted by scattering particle 102 toward the exterior of the catheter body, directed toward photolytic layer 104.

Other types of out-coupling means may also be used, provided that a sufficient amount of light can be redirected, i.e., refracted, to the exterior of the catheter and thus to the photocatalytic layer. Surface texturing, embedded surface particles, and incorporation of bubbles in the catheter body additionally or alternatively serve to facilitate out-coupling.

Figure 12:
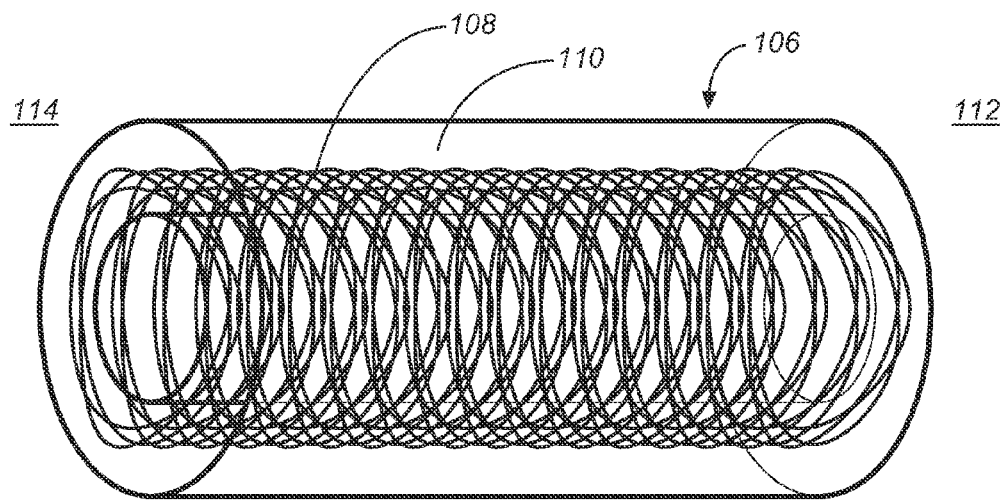
FIG. 12 illustrates a representative segment of an implantable catheter of the invention with an implanted braid shown disposed within the wall of the catheter.

As with scattering particles, any material used for an alternative out-coupling means must have an index of refraction sufficiently different from that of the catheter body in which they are dispersed in order to function effectively. Preferably, the material is substantially transparent to the ultraviolet radiation used in the photocatalytic disinfection process. For instance, other out-coupling means may be disposed within the catheter body in an elongate tubular shape, e.g., as a braid, weave, helix, twist, knit, or the like, in which the individual wires or threads may be individual or bundled, e.g., twisted. Materials for such out-coupling means can generally be selected from materials suitable for the cladding layer, including, by way of example, fluoropolymers, PVC, and amorphous versions of aliphatic polymers such as polyethylene and polypropylene, with fluoropolymer braids, weaves, and the like, such as FEP braids, particularly preferred. FIG. 12 illustrates a representative catheter 106 with an implanted braid 108 shown disposed within catheter body 110 and extending from the distal end 112 of the catheter to the proximal end 114.

Braids, weaves, and the like also as structural reinforcement means, increasing the resistance of the catheter to kinking, breaking, and collapsing. In general, these reinforcement means increase the tear strength of the catheter, the tensile strength of the catheter, and/or the force at break. The tear strength of UV-transparent silicone is on the order of about 80 lbs/in., and although silicones with tear strength up to about 200 lbs/inc can be obtained commercially, these are generally opaque. Accordingly, introduction of a structural reinforcement means into the implantable catheter of the invention is generally preferred.

If scattering particles or a braid- or weave-type structure were to be incorporated into the catheter body so that the approximate density of out-coupling (scattering) material remains constant along the length of the catheter, i.e., from the proximal end where the light is input to the distal end in the patient's body, most of the light introduced into the catheter would be scattered to the exterior of the catheter in the initial segment of the catheter at the proximal end, meaning that little or none of the light would be carried all the way along the length of the catheter to reach the distal end. This would in turn mean that while there would be a high concentration of ROS generated by the photocatalytic layer at the proximal end, there would be very little ROS generated further along, diminishing the ability of the system to inhibit biofilm growth. In order to overcome the problem, the implantable catheter of the invention requires an out-coupling regulating means for ensuring that the amount of out-coupled ultraviolet light is substantially uniform along the length of the catheter from the proximal end to the distal end, to ensure biofilm inhibition along the entire length of the catheter. The substantial uniformity of the outwardly directed light along the entire length of the catheter ensures generation of an approximately constant concentration of ROS along the length of the catheter as well, in the localized region of the catheter surface in the vicinity of a growing or existent biofilm. By "approximately constant" is meant a concentration that does not differ by more than about 50% at any point along the length of the catheter, and typically does not differ by more than about 25%, 15%, or 10% along the length of the catheter.

Figure 13:
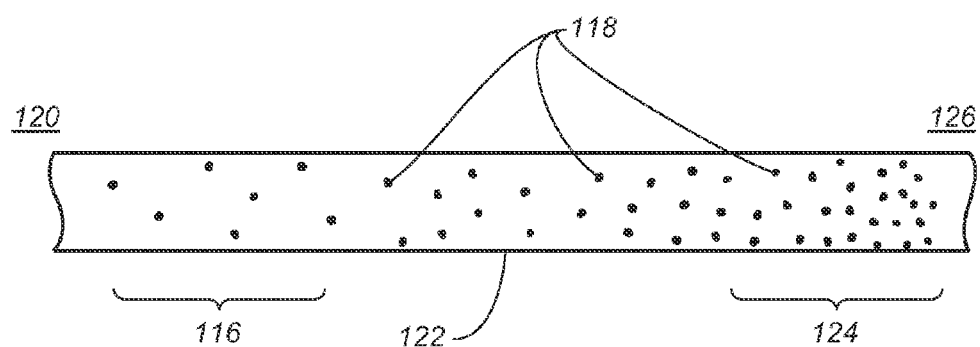
FIG. 13 schematically illustrates a density gradient of scattering particles along the length of the catheter.

The out-coupling regulating means is a built-in density gradient of the out-coupling means in the catheter, such that the density of the out-coupling means gradually increases along the length of the catheter from a low density at the proximal end to a high density at the distal end. For instance, with scattering particles, the density gradient would involve a low particle per volume at the proximal end, increasing axially along the length of the catheter to a high particle per volume at the distal end. This is illustrated in FIG. 13, with a lower density 116 of scattering particles 118 at the proximal end 120 gradually increasing longitudinally along the length of the catheter 122 to a higher density 124 at distal end 126. Generally, the density of scattering particles will increase by a factor of about 2 to about 100 from the proximal end to the distal end, and more typically by a factor of about 5 to about 15. The same principle is applied regardless of the out-coupling means. Incorporation of bubbles in the catheter body, or texturing of the catheter surface done for scattering purposes, is done at low density at the proximal end of the catheter, gradually increasing to a high density at the distal end. Similarly, with an out-coupling means in the form of an incorporated braid, weave, helix, or the like, the structure would be expanded to a low density at the proximal, input end and gradually compressing to a high density compressed state at the distal end of the catheter. Note that "density" in this context refers to the volume of out-coupling material (scattering particle, braid, etc.) per unit volume of catheter body material.

In some embodiments, it may be desirable to include a means for imparting radioopacity to the catheter body to enable visualization of the implanted catheter using medical imaging technology. Radioopacity is required in numerous imaging techniques involving catheter placement and maneuvering, including, by way of example, X-ray, MRI, CT technology, fluoroscopy, or the like. For example, a mesh, e.g., a stainless steel mesh, can be bonded or otherwise affixed to the catheter body, which would be interposed between the catheter exterior and the cladding, if a cladding layer is used. Alternatively, or in addition, a pattern of an inorganic material could be introduced onto the outer catheter surface and the cladding material during manufacture. Barium compounds, such as barium titanate and barium sulfate, are exemplary such materials. Depending on the thickness of the photocatalytic layer material used, the photocatalytic layer can impart some degree of radioopacity as well, e.g., a titanium dioxide thicker than about 100-200 nm. Scattering particles can also impart some radioopacity, e.g., fumed silica particles, barium compounds, and the like.

The implantable catheter of the invention functions in the context of an implantable catheter system that includes a light source and a power source operably connected to and capable of powering the light source. The light source is capable of providing ultraviolet light having a wavelength in the range of about 320 nm to about 387 nm, in order to activate the photocatalysis reaction on the catheter surface, and is optically connected to the catheter in a manner effective to enable irradiation of the catheter body with the ultraviolet light. The light source may be a UV laser, a mercury lamp, or an LED; any source of UV light is suitable or adaptable for the present purpose. In the hospital setting, the light source will most frequent be a UV laser. It will be appreciated that the UV laser and mercury lamp operate at significantly higher power, on the order of 50 mW to about 200 mW, while total power to the UV LED is, by contrast, on the order of 10 mW. In many contexts the LED will be preferred, insofar as with an LED, the device can be powered by a small battery that may be carried or worn by the patient or implanted within the system. The device may also be remotely powered while implanted in a patient, by wirelessly connecting the power source to the light source, as may be enabled by incorporating an inductive powering means in the power source, with the light source provided with a corresponding antenna.

It will be appreciated that in the foregoing embodiments, the interior of the catheter may be longitudinally segmented into two or more lumens as necessary for implementation in a particular medical procedure. For example, one lumen may be sized to receive a guidewire to facilitate proper and exact positioning of the catheter and particularly the distal tip within the patient's body, as may be confirmed during insertion using fluoroscopy (alternatively, the guidewire can be contained in a single-lumen catheter as illustrated in the figures described above). A second lumen may be used to contain an optical fiber used in any of a variety of contexts, including as a means to measure oxygen concentration in the blood.

Manufacture:

A variety of methodologies can be used to fabricate the implantable catheters of the invention. Suitable manufacturing techniques include extrusion and casting. Extrusion is preferred, because it is a more rapid and efficient technique, but casting can be advantageous in introducing and precisely positioning additives such as scattering particles or fibers. In extrusion, a paste is prepared using a precursor or prepolymer to the flexible elastomer that will serve as the catheter body. The precursor or prepolymer to the flexible elastomer is cross-linkable with heat, ultraviolet radiation, or chemically, using a cross-linking agent. With silicone catheters, as an example, the paste would contain a crosslinkable siloxane polymer or prepolymer that is readily curable, to form the catheter body. Depending on the crosslinkable siloxane polymer or prepolymer, an added crosslinking agent might be necessary. As used herein, the term "crosslinkable" refers to a polysiloxane having reactive or functional groups that enable thermal, photochemical, or chemical crosslinking Silicone polymers of this description are generally known and commercially available. By way of illustration, mention may be made of poly(dimethylsiloxane) (PDMS) and fluoroalkylmethyl siloxane. A particularly preferred crosslinkable polysiloxane is PDMS, which is characterized as possessing high strength and elasticity. The extruded catheter is then treated as necessary, e.g., with light and/or heat and/or moisture, to cure the polysiloxane and thereby form the catheter body. With catheters fabricated from extrudable materials other than silicone, a similar manufacturing process would be used.

The photocatalytic layer, e.g., particulate titanium oxide, zinc oxide, alumina, or the like, can be incorporated in any number of ways. If extrusion is used to prepare the catheter body, particulate titania or the like may be dusted on while the silicone or other catheter material is still relatively soft and tacky, so that the photocatalytic particles are adsorbed onto the catheter surface. A titania or other photocatalytic layer can also be provided on the catheter surface by co-extrusion of the polymeric material used for the catheter body per se along with the photocatalytic material. Another suitable method involves introduction of the photocatalytic material after catheter fabrication by swelling the catheter in a solvent, e.g., tetrahydrofuran, methylene chloride, toluene, isopropanol, etc., for up to several hours, and then dipping the catheter in a suspension of titania in a like solvent to absorb the photocatalytic particles, followed by removal of the solvent using conventional means. Another method employs a tethering technique, wherein the silicone surface is activated (e.g., using plasma treatment in an oxidizing atmosphere), followed by treatment of the activated surface with a reactive silane, which in turn can tether titania or the like by immersion in a solution of the particulate photocatalytic material. If a fluoropolymer or other cladding layer is to be employed so that the exterior of the catheter is then composed of the fluoropolymer instead of silicone (for example), the photocatalytic material must generally be separately incorporated as a layer on the cladding surface, typically at a high temperature just slightly below the melting point of the fluoropolymer or other cladding material, to allow the material to soften and become sufficiently tacky to allow adsorption of photocatalytic particles.

The out-coupling means will be incorporated into the implantable catheter during extrusion or casting, along with the selected means for adding radioopacity, if desired. Scattering particles or fibers can be added into the curable polymeric material selected for the catheter body during extrusion or casting. With a braid, weave, or the like, the catheter body may be manufactured so that the element is incorporated in the catheter wall using conventional means.

Operation:

The implantable catheter system is activated to begin biofilm inhibition by irradiation of the catheter body using ultraviolet light of a wavelength to activate the photocatalytic layer, e.g., about 380-387 nm for a titanium dioxide layer, at a power density in the range of about 1 $\mu W/cm^2$ to about 10 $mW/cm^2$. Low levels, on the order of about 1 $\mu W/cm^2$ to about 1 $mW/cm^2$, generally in the range of about 1 $\mu W/cm^2$ to about 10 $\mu W/cm^2$, can deter biofilm growth, and thus be used effectively in the preventive context. For biofilm destruction, e.g., after a biofilm infection has been detected, higher levels are used, in the range of about 10 $\mu W/cm^2$ to about 10 $mW/cm^2$. In the latter case, activation via irradiation may be done intermittently at approximately regular intervals for a time period in the range of about 2 minutes to about 2 hours, typically about 15 minutes to about 1 hour. The prophylactic mode, however, in which biofilm growth is deterred, and lower power density levels are used, can involve continuous irradiation over a time period of at least 72 hours.

Ideally, the information pertaining to actual use of a single implantable catheter system in a patient can be stored and tracked. Such information includes, for example, the installation date of the catheter, the access dates of the catheter, the activation dates and times, duration of use, and the like. Information on the activation pattern of a catheter, e.g., prophylactic at a low level versus activation at a high level once a biofilm has been detected, can yield critical information relevant to a determination of what therapies work best for which patients. To enable gathering of the aforementioned information, the implantable catheter system should include an internal clock that can store date and time, a sensor (e.g., a capacitive or resistive sensor) in the catheter to determine when its fluid connector is accessed, a means for monitoring activation patterns and power used, and a means to communicate with a data output device and optionally through a wired or wireless communication channel with a hospital network. The pertinent information can thereby be made known to medical personnel through a dashboard, the patient's electronic medical record (EMR) or a parallel system or application. The information provided will serve as a quality control for the use of the catheter and a source of new knowledge to optimize the clinical use of the catheter and reduce the morbidity and mortality due to biofilm infections. More specifically, the information system will provide the following benefits: provide control over the number of times the implantable catheter is accessed and the length of time it is used; produce new knowledge to determine what pattern of use results in better outcomes for a patient; avoid unnecessary and costly removal of catheters when catheter infection is suspected; and over time, optimize the use of activation patterns of the catheter so as to result in optimal patient outcomes.

Utility:

The implantable catheter of the invention finds utility in a diverse plurality of contexts in which a catheter is implanted in a patient. In general, the method and implantable catheter of the invention find utility in connection with a wide variety of catheter types, e.g., with arterial catheters, central venous catheters, dialysis tubing, endrotracheal tubes, enteral feeding tubes, Foley catheters, gastrostomy tubes, hemodialysis catheters, nasogastric tubes, nephrostomy tubing, pulmonary artery catheters, tracheotomy tubes, tympanostomy tubes, shunts, umbilical catheters, urinary catheters, and the like.

Particularly important areas of use are medical procedures that require repeated and prolonged access to a patient's vascular system, for example, to carry out transfusions, administer antibiotics, drugs, nutrition, or chemotherapy agents to the bloodstream, or to purify a patient's blood. For example, central venous catheters normally remain implanted for a longer period of time than other venous catheters, especially when there is an extended and ongoing need for their use, such as the administration of total parenteral nutrition in a chronically ill patient. As another example, during treatment of diabetic patients, blood is removed for filtering and purification externally to the body; typically, access is obtained through a vein or artery.

Cumulative damage to the skin and vascular walls caused by repeated punctures makes it impractical to introduce a new catheter into the patient's venous system at regular intervals. Use of the implantable catheter of the invention eliminates the need for repeated removal and insertion of catheters, as the infecting microorganisms in biofilms can be killed and the catheter thus disinfected without removal from the patient's body.

In use, then, the implantable catheter is inserted through the patient's skin so that the distal end remains under the skin, within the patient's body, while the proximal end extends outside the body for connection to an external line. The distal end generally enters a patient's vein, and the proximal end is connected through an external line to a device used to receive, supply, and/or process medical fluids, such as blood. The outer surface of the catheter body is exposed to the environment surrounding the catheter. For example, the outer surface may be in contact with the contents of a body lumen into which the catheter has been inserted.

It will be appreciated by those skilled in the art that the invention described herein can be implemented in a range of contexts in which a device is implanted in the body of a patient, in which case the implant surfaces are at risk for infection with biofilm microorganisms. Such implants include, without limitation, stents, including biliary, hepatic, and esophageal stents, orthopedic prostheses, pins, joints, and other implants, dental implants, intracardiac prostheses, vascular prostheses including prosthetic heart valves, artificial hearts, and pacemakers.

EXPERIMENTAL

Materials and Methods

Strains and Growth Conditions: Throughout the study *Pseudomonas aeruginosa* (PAO1) tagged with green fluorescent protein (Gfp) (Tn7::Gfp tagged, Amp$^r$, Km$^r$) was used. Strains were grown in M9 media with addition of 1 mM $MgCl_2$, 0.1 mM $CaCl_2$, and 0.01 mM $FeCl_3$. Media were adjusted to physiological/blood stream NaCl concentrations of 0.9%. In addition, 1 mM glucose was added as the sole carbon source for batch experiments, and 0.01 mM glucose was added for flow chamber experiments. When required, antibiotics were added at final concentrations of 100 µg/ml Ampicillin and 20 µg/ml Gentamycin. Visualization of live and dead cells was carried out by staining with Baclight live dead stain from Molecular Probes, Inc. (Eugene, Oreg., USA) showing live cells by green fluorescence and dead cells by red fluorescence. When Gfp was constitutively expressed in cells (e.g., for PAO1), live cells are represented by green fluorescence from Gfp.

Flow Chamber Experiments: Biofilms were grown at 30° C. in flow chambers. The flow system was assembled and prepared as described by (Christensen et al., 1998), (Sternberg and Tolker-Nielsen, 2006). The$_{[J1]}$substratum consisted of a microscope glass coverslip (st1; Knittel Glaser, Braunschweig, Germany) mounted with a $TiO_2$-coated polyethylene terephthalate (PET) surface. Each channel was supplied with a flow of 3 ml/h of M9-medium containing the appropriate carbon source. Flow cells were inoculated with the strain of interest grown for 18 h in LB medium and diluted to OD 0.01 prior to inoculation. After having stopped the media flow the flow channels were inverted and 250 µl of the diluted mixture was carefully injected into each flow channel using a small syringe. After 1 h the flow channel was inverted and the flow was resumed using a Watson Marlow 205S peristaltic pump (Watson Marlow Inc., Wilmington, Mass.). The mean flow velocity in the flow cells was 0.2 mm/s. A scaled up flow cell was developed and used for monitoring growth and killing efficiencies on typical catheter-length tubes. This flow cell had the dimensions of 4×30×160 mm. In order to follow the killing of cells using activated photocatalysis of the titania surface vis-à-vis the spatial localization of single cells and biofilm developed in the flow channels, cells were stained with live dead stain 15 min prior to inspection using confocal microscopy.

Two Biofilm Systems: Throughout these studies, a static system was used in which a titania-coated silicone tube was mounted on the bottom of 6 well Petri dishes, with inspection taking place directly in the well using dipping lens objectives. In this system, biofilms were allowed to develop for 5-6 h. This system allowed for development of a thin monolayer biofilm at the substratum with beginning small micro colony structures. A second system used was a flow system that allowed for mature biofilm development over several days and treatment at different time points during biofilm maturation. In both systems, it was possible to perform comparative testing on established biofilms.

Microscopy and Image Analysis: All microscopic observations and image acquisition was performed on a TCDSP2 scanning confocal laser microscope, CLSM (Leica Lasertechnik GmbH, Heidelberg, Germany) equipped with an argon/krypton laser and detectors and filter sets for simultaneous monitoring of Syto9/Gfp (excitation 488 nm, emission 517 nm) and propidium iodide (excitation 543 nm, emission 565 nm). Images were obtained using a 63x/1.4 Plan-APO-Chromat, a 63x/0.90w HCX-APO and a 20x/0.50w HCX-APO objective. Multichannel simulated fluorescence projection (SFP, a shadow projection) images and vertical cross sections through the biofilm were generated by using the IMARIS software package (Bitplane AG, Zürich, Switzerland). Images were further processed for display by using Photoshop software (Adobe, Mountain View, Calif.).

Image Acquisition for Quantification Using COMSTAT: For quantification of biomass and calculation of % of dead cells, independent biofilm experiments were performed acquiring image stacks randomly of the respective biofilm samples. Images were further treated using COMSTAT (Heydorn et al. (October 2000) *Microbiology* 146 (Pt 10):23950407. By viewing the images from the confocal microscope and quantifying the relative amounts of green cells and red cells at regular intervals, one can calculate biomass and monitor biofilm growth. The fraction of dead cells can thereby be deduced throughout the electrochemical process.

Results

Figure 14:
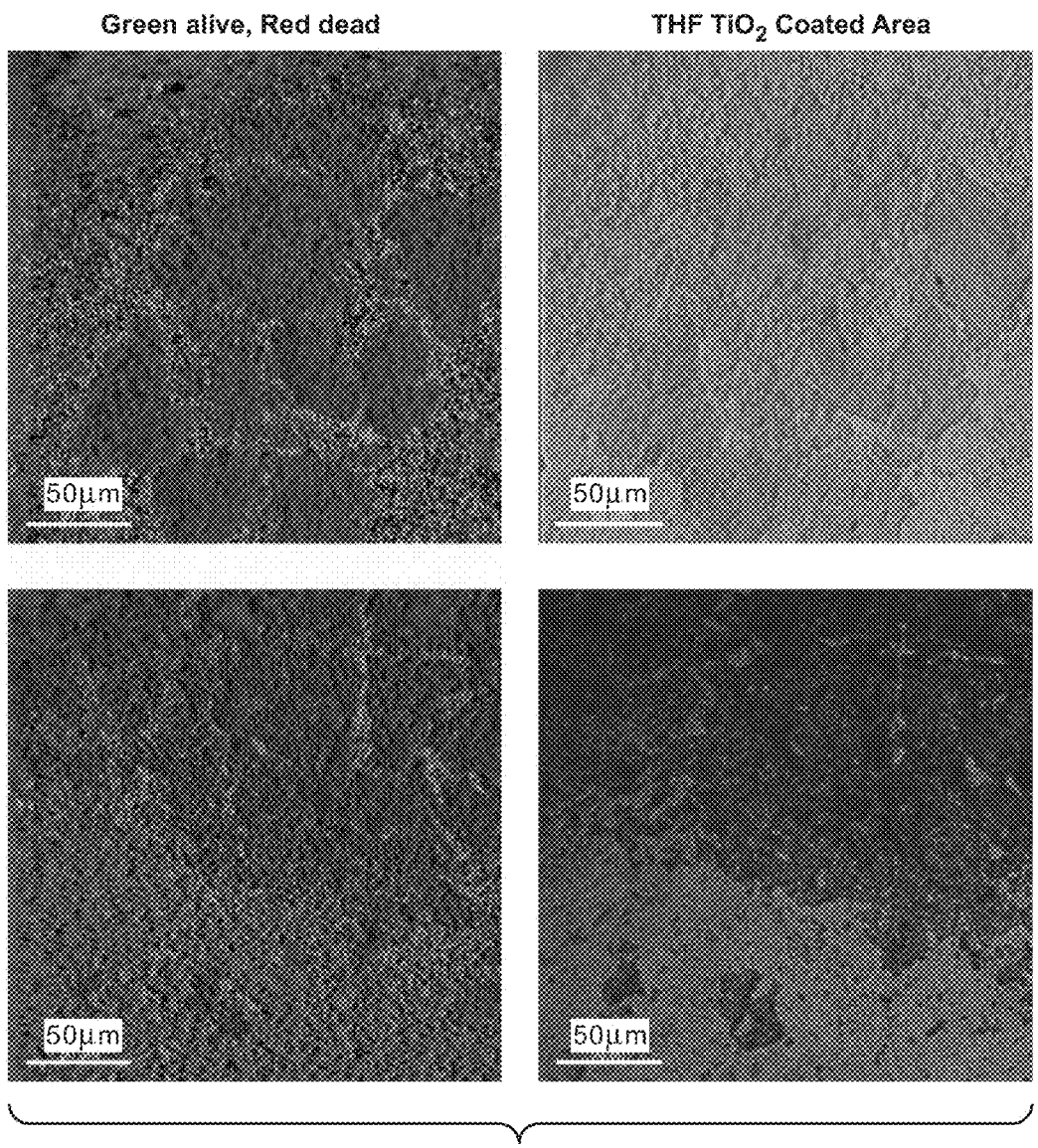
FIG. 14 shows images obtained using confocal microscopy of a 5 h Gfp-tagged *P. aeruginosa* biofilm grown in minimal glucose media on a $TiO_2$-coated surface that was exposed for 3 h to 0.1 mW/cm² UVA light.

The images obtained using confocal microscopy and shown in FIGS. 14-17 and 19 confirm the efficacy of the photocatalytic method and system of the invention in inhibiting biofilm growth:

FIG. 14 shows images obtained using confocal microscopy of a 5 h Gfp-tagged *P. aeruginosa* biofilm grown in minimal glucose media on a $TiO_2$-coated surface that was exposed for 3 h to 0.1 mW/cm$^2$ UVA light. The images show live (green) cells and dead (red) cells after treatment as well as a transmitted light image indicating the specific location $TiO_2$ on the surface. There is a clear association demonstrated between the presence of the photocatalytic TiO$_2$ coating and efficient biofilm destruction. If light intensity is limited in a 3 h illumination process, as was the intensity used here, only biofilm on the efficient coating areas will be killed. With higher light intensity, killing extends as well to areas in close proximity to the coating. Live cells are represented in green (from Gfp expression in viable cells) and dead cells are shown in red (following propidium iodide staining).

Figure 15:
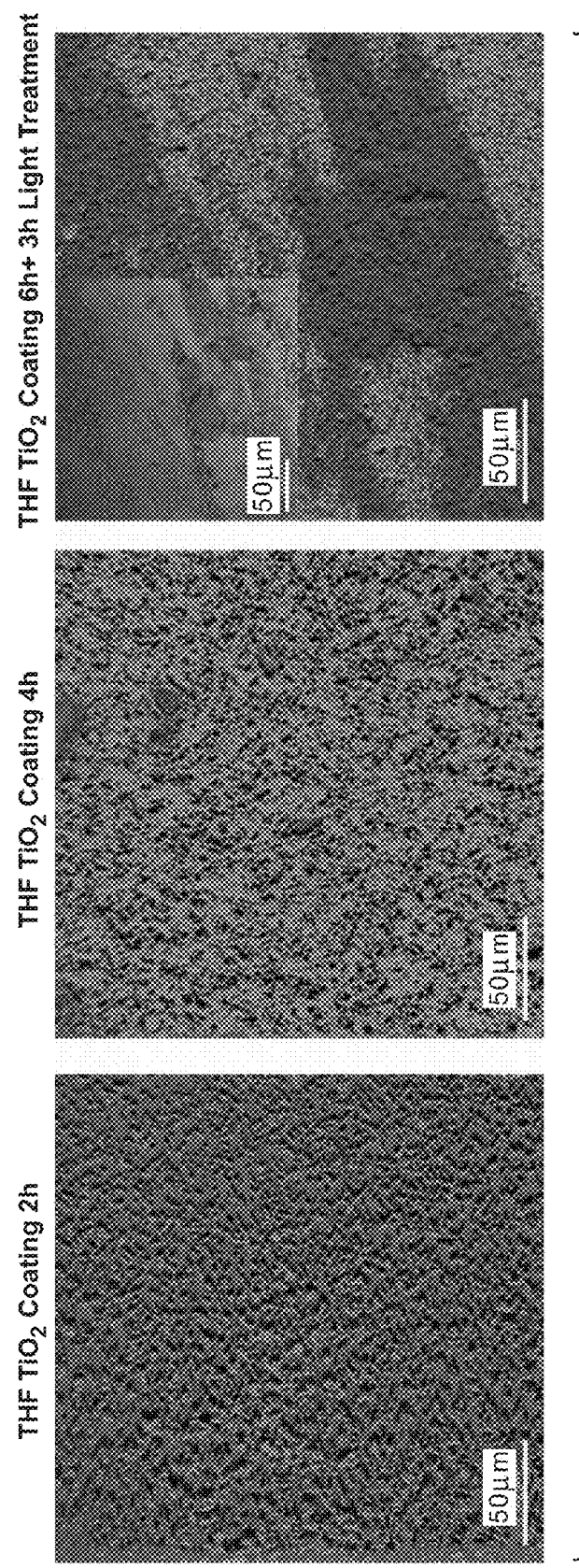
FIG. 15 shows images obtained using confocal microscopy of Gfp-tagged *P. aeruginosa* biofilm development after 2 h, 4 h and 6 h of growth in glucose minimal media followed by 3 h treatment of the mature 6 h biofilm with 0.1 mW/cm² UVA light.

FIG. 15 shows images obtained using confocal microscopy of Gfp-tagged *P. aeruginosa* biofilm development after 2 h, 4 h and 6 h of growth in glucose minimal media followed by 3 h treatment of the mature 6 h biofilm with 0.1 mW/cm$^2$ UVA light. The two images on the left show live (green) cells and dead (red) cells after treatment, while the third is a transmitted light image showing the specific location of TiO$_2$ on the surface. Again, a clear association was demonstrated between the presence of the photocatalytic coating and efficient biofilm destruction.

Figure 16:
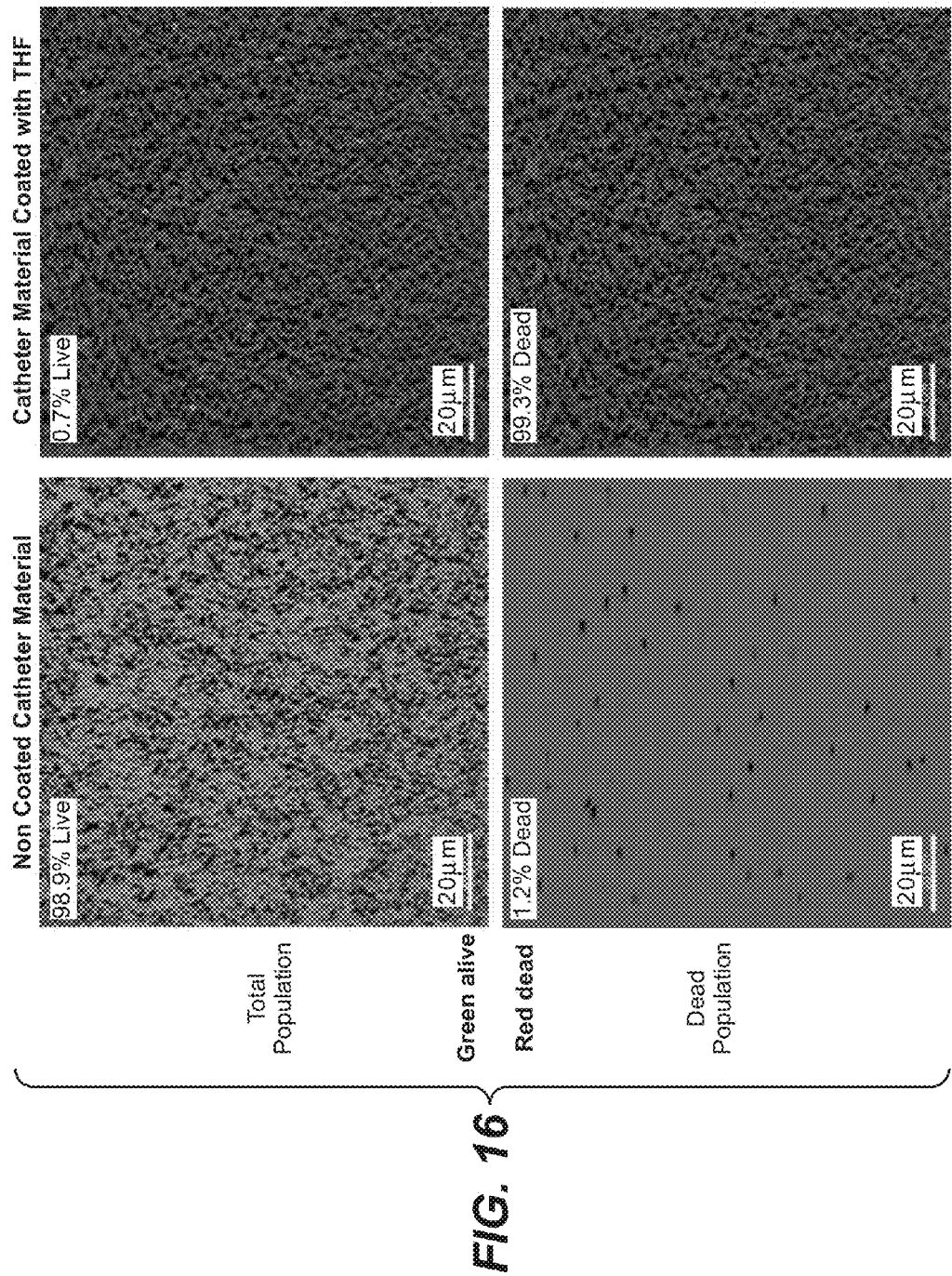
FIG. 16 shows images obtained using confocal microscopy of Gfp-tagged *P. aeruginosa* biofilm development after 5 h growth in glucose minimal media followed by 1 h treatment with 10 mW/cm² UVA light. The photocatalytic destruction of the biofilm was confirmed to be highly efficient, with only 0.7% of the cells alive on the $TiO_2$-coated surface after 1 h, compared with 98.9% of the cells on the uncoated surface.

FIG. 16 compares images obtained using confocal microscopy of Gfp-tagged of Gfp-tagged *P. aeruginosa* biofilm development after 5 h growth in glucose minimal media followed by 1 h treatment 10 mW/cm$^2$ UVA light. The photocatalytic destruction of the biofilm was confirmed to be highly efficient, with only 0.7% of the cells alive on the TiO$_2$-coated surface after 1 h, compared with 98.9% of the cells on the uncoated surface.

Figure 17:
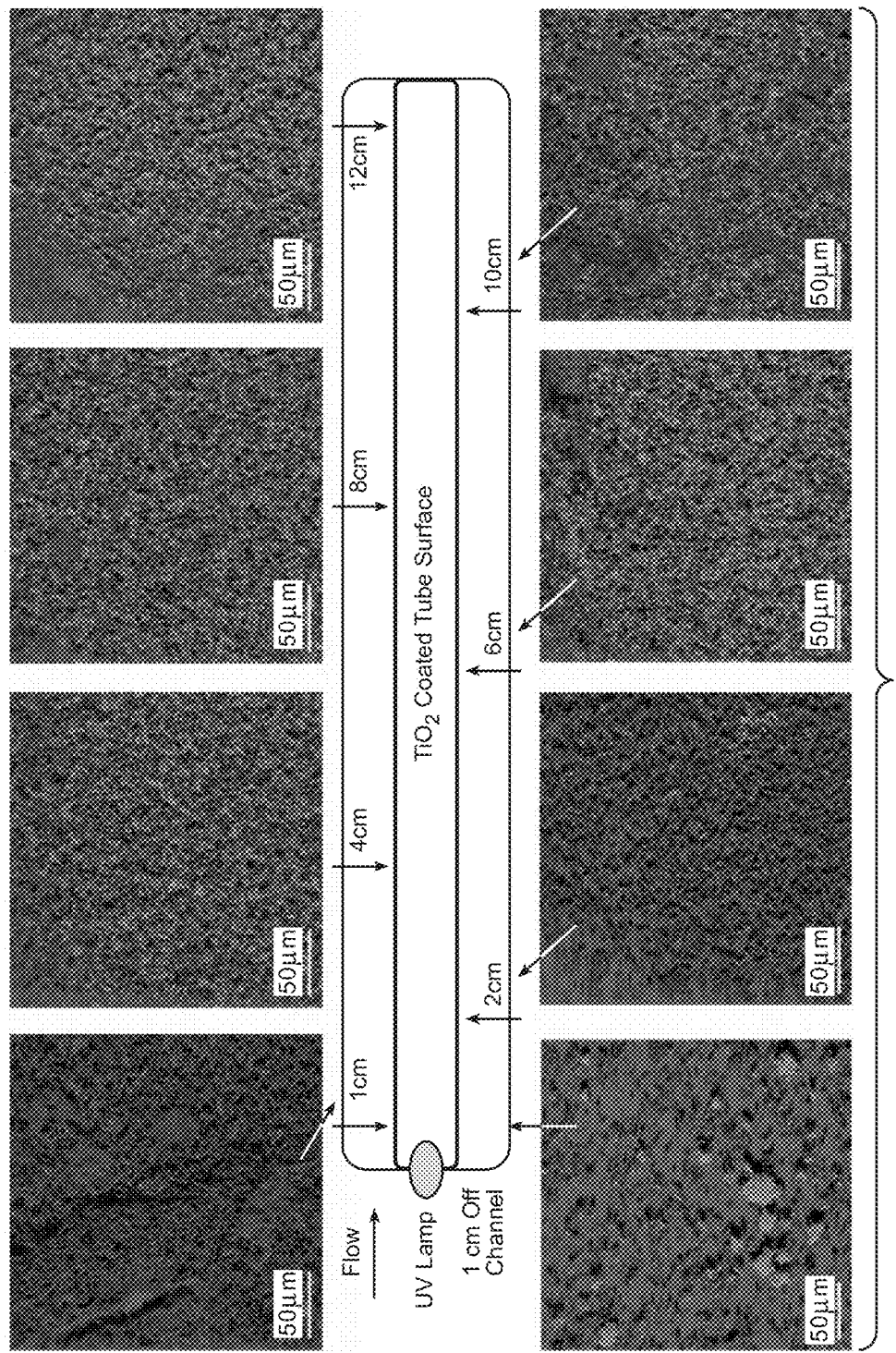
FIG. 17 shows images obtained using confocal microscopy of a Gfp-tagged *P. aeruginosa* biofilm grown in a 12 cm long flow chamber in which a $TiO_2$-coated silicone tube was inserted, and irradiated with UVA light after three days of biofilm development.

FIG. 17 shows images obtained using confocal microscopy of a Gfp-tagged *P. aeruginosa* biofilm grown in a 12 cm long flow chamber in which a TiO$_2$-coated silicone tube was inserted. A light source was connected to one end of the silicone tube, and a flow of glucose minimal media was continually supplied to biofilm developing on the surface. After 3 days of biofilm development UVA light was directed in to the silicone tube to activate the TiO$_2$ surface. The inlet level of light was 10 mW/cm$^2$. The images show live (green) cells and dead (red) cells after treatment for 1 h. Live cells are represented in green (from Gfp expression in viable cells) and dead cells are shown in red (following propidium iodide staining) The images show a clear correlation between the degree of biofilm destruction and distance from the light source, as evidenced by the number of live versus dead cells seen along the length of the irradiated tube.

Figure 18:
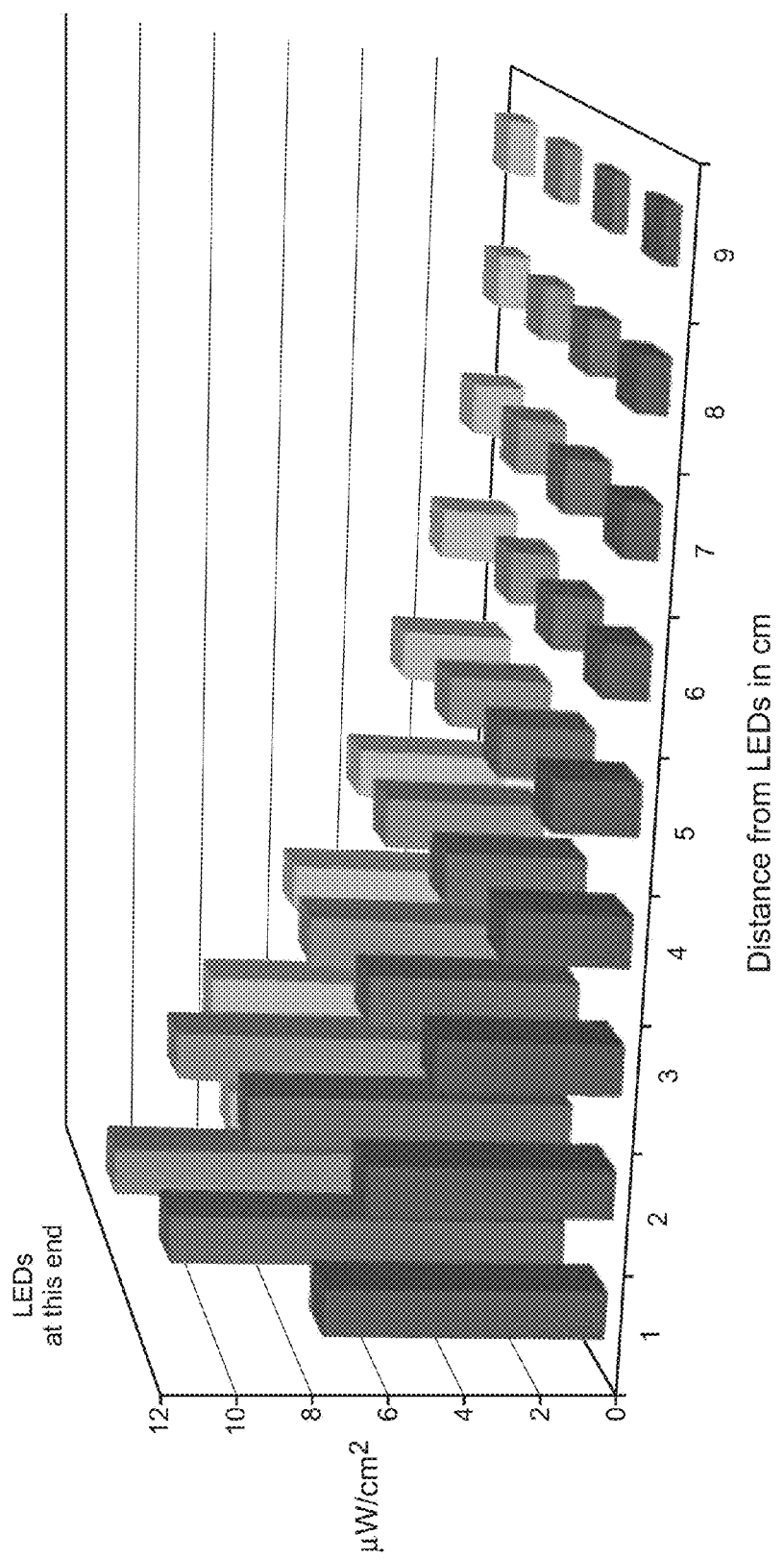
FIG. 18 is a diagram showing in three-dimensional graph form the light distribution along a silicon tube irradiated at 10 mW/cm², with four repeated measurements taken at different distances from the light inlet.

FIG. 18 is a diagram showing in three-dimensional graph form the light distribution along a silicon tube irradiated at 10 mW/cm$^2$, with four repeated measurements taken at different distances from the light inlet.

Figure 19:
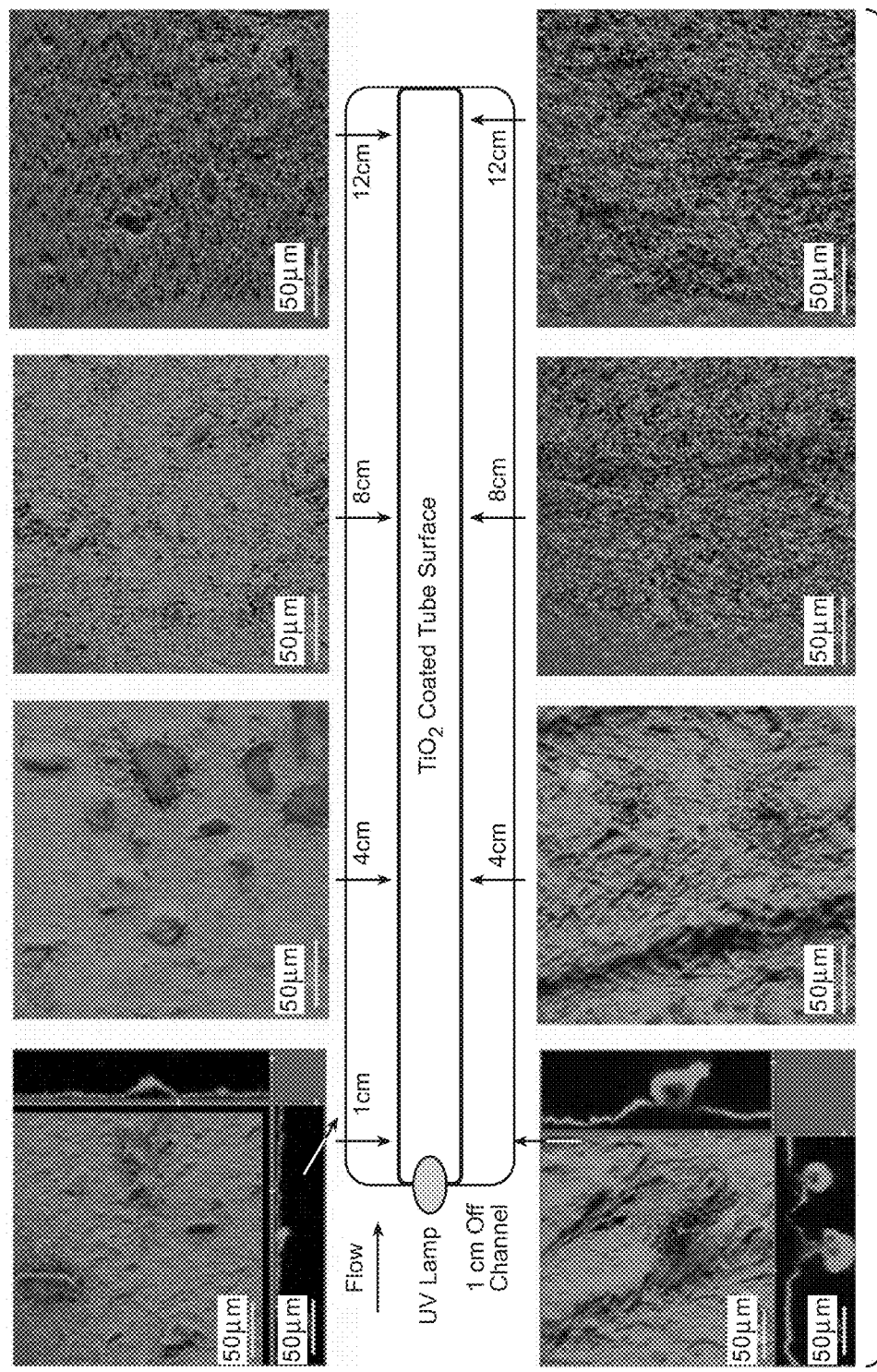
FIG. 19 shows images obtained using confocal microscopy of a Gfp-tagged *P. aeruginosa* biofilm grown for 3 days in a 12 cm long flow chamber in which a $TiO_2$-coated silicone tube was inserted, with no photocatalytic activation.

FIG. 19 shows images obtained using confocal microscopy of a Gfp-tagged *P. aeruginosa* biofilm grown in a 12 cm long flow chamber in which a TiO$_2$-coated silicone tube was inserted. A light source was connected to one end of the silicone tube, and a flow of glucose minimal media was continually supplied to biofilm developing on the surface. After 3 days of biofilm development, these figures show biofilm in different areas of the silicon tube without activation of the TiO$_2$ surface.

The images show live (green) cells and dead (red) cells. Without photocatalytic activation of the TiO$_2$ surface, the biofilm continues to thrive.

Figure 20B:
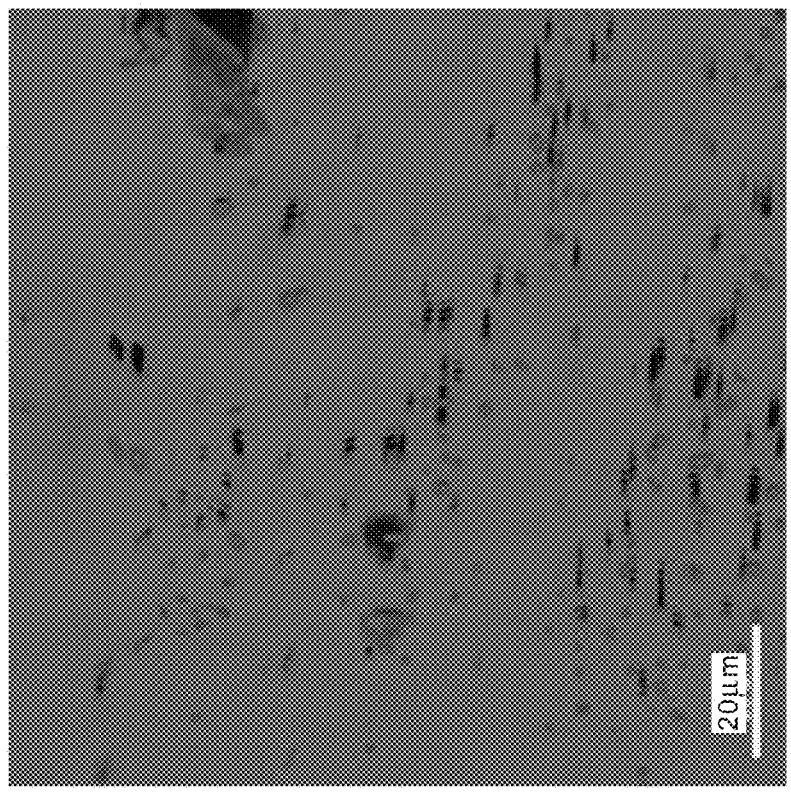
FIG. 20B shows the image obtained of the same silicone tube after irradiation with UVA light for 2 h at 0.8 mW/cm².
Figure 20A:
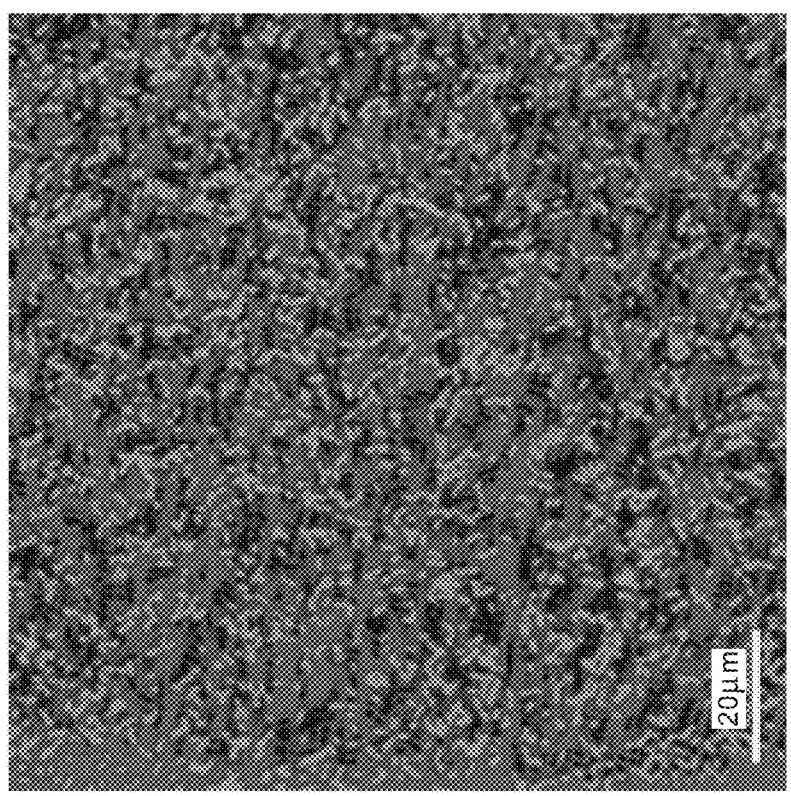
FIG. 20A shows the image obtained using confocal microscopy of a Gfp-tagged *P. aeruginosa* biofilm grown for 2 h on a 20 cm long coated silicone tube.
Figure 21:
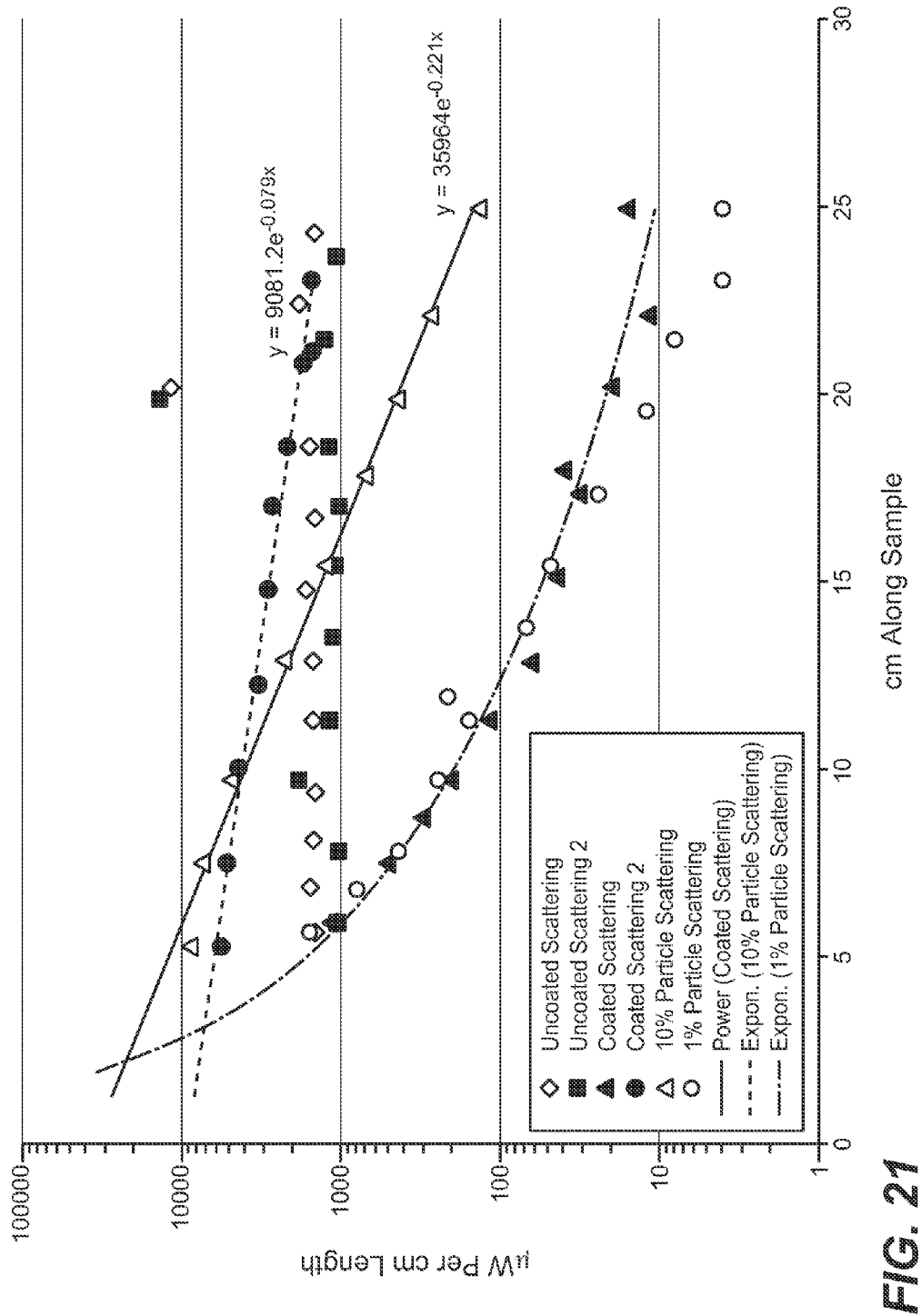
FIG. 21 is a graph showing the results of an experiment comparing scattered light output from uncoated silicone tubes, tubes coated with a photocatalytic layer, and tubes coated with a photocatalytic layer and containing scattering particles.

FIG. 20A shows the image obtained using confocal microscopy of a Gfp-tagged *P. aeruginosa* biofilm grown for 2 h on a 20 cm long coated silicone tube. FIG. 20B shows the image obtained of the same silicone tube after irradiation with UVA light for 2 h at 0.8 mW/cm$^2$. Both images are from the tip of the silicone tube 20 cm away from the light source and demonstrate that light can be transported in a catheter-like silicone tube and kill biofilm at a distance from the light source. Live cells are represented in green (from Gfp expression in viable cells) and dead cells are shown in red after propidium iodide staining Density Studies:

In this experiment, four different sample types of silicone tubing (approximately 6 mm diameter, 30 cm long) were compared with respect to scattered light output along the length of the tube. Approximately 150 mW of UVA light was directed into one end of the tube, and the light output was measured along the sample length. The results are shown in the graph of FIG. 21. The samples were as follows: (1) uncoated medical grade silicone, two experiments (represented in FIG. 21 as diamonds and squares); (2) medical grade silicone coated with titanium dioxide particles (Aeroxide® TiO$_2$ P-25, Evonik Industries) by rubbing a dispersion of TiO$_2$/tetrahydrofuran (THF) on to the tube to provide a relatively even TiO$_2$ coating, two experiments (represented in FIG. 21 as triangles and circles); (3) medical grade silicone coated as in (2) with scattering particles incorporated into the silicone; and (4) medical grade silicone also with scattering particles incorporated into the silicone, but at 10% of the density used in (3).

For sample (1), each centimeter of length was found to emit approximately 1.5 mW of light (although a small spike may be seen on the graph due to a bubble in the sample), with the majority of the light remaining inside the sample to be emitted at the far end. For sample (2), which had a slightly filmy-looking surface as a result of the TiO$_2$ particles, there was an enormous amount of light out-coupling (scattering), resulting in about a four-order-of-magnitude variation in emitted light intensity over the length of the sample. Samples (3) and (4) show how the out-coupling percentage can be adjusted by changing the density of scattering particles within the sample instead of on the surface. The slopes of these two lines can be used to determine where along the catheter to change from 1 to 10 percent concentration of scattering particle-doped silicone. Compared to the untreated samples, the samples with the scattering particles allowed the emitted light along the length of the catheter to be increased at least 5× and held relatively constant, resulting in less "wasted" light out the far end of the catheter.

All journal articles and patents and patent application publications cited herein are incorporated by reference in their entirety.

The foregoing description is intended to illustrate various aspects of the instant technology. It is not intended that the examples presented herein limit the scope of the appended claims. The invention now being fully described, it will be apparent to one of ordinary skill in the art that many changes and modifications can be made thereto without departing from the spirit or scope of the appended claims.

We claim:

1. An implantable catheter that can be photocatalytically disinfected without removal from a patient's body, comprising:
    an elongate catheter body of predetermined length having a proximal end, a distal end, at least one lumen extending through the catheter body and adapted to transport fluid from the proximal end to the distal end, an outer surface on the exterior of the catheter body, and an inner surface on the interior of the lumen;
    an outer photocatalytic layer on the outer surface that undergoes a photocatalysis reaction upon irradiation with ultraviolet light to generate reactive oxygen species;
    an out-coupling means for facilitating out-coupling of ultraviolet light directed into the catheter at the proximal end so that along the length of the catheter a first fraction of the light is refracted toward the catheter surfaces and thus toward the outer photocatalytic layer, thereby activating the photocatalysis reaction;

wherein the out-coupling means has a density gradient that increases axially along the length of the catheter from the proximal end to the distal end for ensuring that the amount of out-coupled ultraviolet light is substantially uniform along the length of the catheter from the proximal end to the distal end.

2. The implantable catheter of claim 1, wherein the outer photocatalytic layer is comprised of particulate crystalline titanium dioxide selected from anatase, brookite, rutile, and combinations thereof.

3. The implantable catheter of claim 2, wherein the crystalline titanium dioxide comprises at least 50% anatase.

4. The implantable catheter of claim 3, wherein the crystalline titanium dioxide comprises has a particle size in the range of about 10 nm to about 300 nm.

5. The implantable catheter of claim 3, wherein the particle size is in the range of about 100 nm to about 300 nm.

6. The implantable catheter of claim 1, wherein the outer photocatalytic layer has a thickness in the range of about 20 nm to 1 μm.

7. The implantable catheter of claim 1, wherein the outer photocatalytic layer has a thickness in the range of about 20 nm to about 200 nm.

8. The implantable catheter of claim 1, wherein the outer photocatalytic layer is embedded in the outer surface of the catheter and thus integral therewith.

9. The implantable catheter of claim 1, wherein the catheter body comprises a flexible elastomeric material that is substantially transparent to ultraviolet radiation.

10. The implantable catheter of claim 9, wherein the flexible elastomeric material comprises a silicone polymer substantially free of unsaturated bonds.

11. The implantable catheter of claim 1, wherein the out-coupling means comprises scattering particles dispersed in the catheter body along the length thereof.

12. The implantable catheter of claim 1, wherein the out-coupling means comprises a tubular reinforcing element in the catheter body that extends from the proximal end to the distal end and comprises a material that is substantially transparent to the ultraviolet light.

13. The implantable catheter of claim 12, wherein the tubular reinforcing element comprises a braid.

14. The implantable catheter of claim 13, wherein the tubular reinforcing element comprises a helix or weave.

15. The implantable catheter of claim 12, wherein the tubular reinforcing element also serves as a structural support and increases the tear strength of the catheter body.

16. The implantable catheter of claim 12, wherein the tubular reinforcing element is comprised of a material selected from fluoropolymers, poly(vinyl chloride), polyethylene, and polypropylene.

17. The implantable catheter of claim 16, wherein the tubular reinforcing element is comprised of a fluoropolymer.

18. The implantable catheter of claim 17, wherein the fluoropolymer comprises a fluorinated ethylene propylene (FEP) resin.

19. The implantable catheter of claim 17, wherein the fluoropolymer comprises a perfluoroalkoxy copolymer (PFA) resin.

20. The implantable catheter of claim 1, wherein the out-coupling means comprises bubbles in the catheter body along the length thereof extending from the proximal end to the distal end.

21. The implantable catheter of claim 1, wherein the out-coupling means comprises the texturing of the outer wall of the catheter body along the length thereof in a manner that increases the extent of out-coupling from the proximal end to the distal end.

22. The implantable catheter of claim 11, wherein the out-coupling means comprises incorporation of the scattering particles in a density gradient that increases axially along the length of the catheter from the proximal end to the distal end.

23. The implantable catheter of claim 22, wherein the density of scattering particles increases by a factor of about 2 to about 100 from the proximal end to the distal end.

24. The implantable catheter of claim 23, wherein the density of scattering particles increases by a factor of about 5 to about 15 from the proximal end to the distal end.

25. The implantable catheter of claim 12, wherein the out-coupling means comprises incorporation of the tubular reinforcing element in a density gradient that increases axially along the length of the catheter from the proximal end to the distal end.

26. The implantable catheter of claim 11, further including an additional out-coupling means in the form of a tubular reinforcing element in the catheter body that extends from the proximal end to the distal end and comprises a material that is substantially transparent to ultraviolet light.

27. The implantable catheter of claim 1, further including an inner photocatalytic layer on the inner surface that undergoes a photocatalysis reaction upon irradiation with ultraviolet light to generate reactive oxygen species.

28. The implantable catheter of claim 27, wherein the outer photocatalytic layer and the inner photocatalytic layer are comprised of the same material.

29. The implantable catheter of claim 28, wherein the outer photocatalytic layer and the inner photocatalytic layer are comprised of particulate crystalline titanium dioxide selected from anatase, brookite, rutile, and combinations thereof.

30. The implantable catheter of claim 1, further including a light confinement means for ensuring that a second portion of the light is internally reflected and thereby continues to travel axially through the length of the catheter to the distal end.

31. The implantable catheter of claim 30, wherein the light confinement means comprises a cladding layer interposed between the outer surface of the catheter body and the photocatalytic layer.

32. The implantable catheter of claim 31, wherein the cladding layer is comprised of a material having a lower index of refraction than the catheter body.

33. The implantable catheter of claim 32, wherein the cladding layer has a thickness in the range of about 0.002 mm to about 0.5 mm.

34. The implantable catheter of claim 33, wherein the cladding layer has a thickness in the range of about 0.05 mm to about 0.2 mm.

35. The implantable catheter of claim 1, further including a structural reinforcing means for increasing the tear strength of the catheter, the tensile strength of the catheter, the force at break, or any combination thereof.

36. The implantable catheter of claim 1, further including a means for imparting radioopacity to the catheter body to enable visualization of the implanted catheter using medical imaging technology.

37. The implantable catheter of claim 1, wherein the out-coupling means, impart additional radioopacity to the catheter body.

38. The implantable catheter of claim 1, wherein the catheter body is adapted to carry ultraviolet light from the proximal end along its length to the distal end.

39. The implantable catheter of claim 38, further including an additional means for carrying ultraviolet light from the proximal end along its length to the distal end.

40. The implantable catheter of claim 39, wherein the additional light carrying means comprises at least one flexible, substantially UV-transparent fused silica rod, wherein the rod is embedded in the catheter body and extending along the length of the catheter from the proximal end to the distal end, or the rod is wrapped around the catheter in a braid formation or in single or multiple helices.

41. The implantable catheter of claim 39, wherein the additional light carrying means comprises an aqueous liquid in one or more channels in the catheter body that extend along the length of the catheter from the proximal end to the distal end.

42. An implantable catheter that can be photocatalytically disinfected without removal from a patient's body, comprising:
    an elongate catheter body of predetermined length having a proximal end, a distal end, at least one lumen extending through the catheter body and adapted to transport fluid from the proximal end to the distal end, an outer surface on the exterior of the catheter body, and an inner surface on the interior of the lumen;
    an inner photocatalytic layer on the inner surface that undergoes a photocatalysis reaction upon irradiation with ultraviolet light to generate reactive oxygen species;
    an out-coupling means for facilitating out-coupling of ultraviolet light directed into the catheter at the proximal end so that along the length of the catheter a first fraction of the light is refracted toward the catheter surfaces and thus toward the inner photocatalytic layer, thereby activating the photocatalysis reaction;
    wherein the out-coupling means has a density gradient that increases axially along the length of the catheter from the proximal end to the distal end for ensuring that the amount of out-coupled ultraviolet light is substantially uniform along the length of the catheter from the proximal end to the distal end.

43. An implantable catheter system, comprising:
    an implantable catheter that can be photocatalytically disinfected without removal from a patient's body, which comprises: an elongate catheter body of predetermined length having a proximal end, a distal end, at least one lumen extending through the catheter body and adapted to transport fluid from the proximal end to the distal end, an outer surface on the exterior of the catheter body, and an inner surface on the interior of the lumen; an outer photocatalytic layer on the outer surface that undergoes a photocatalysis reaction upon irradiation with ultraviolet light to generate reactive oxygen species; an out-coupling means for facilitating out-coupling of ultraviolet light directed into the catheter at the proximal end so that along the length of the catheter a first portion of the light is refracted toward the catheter surfaces and thus toward the outer photocatalytic layer, thereby activating the photocatalysis reaction; wherein the out-coupling means has a density gradient that increases axially along the length of the catheter from the proximal end to the distal end for ensuring that the amount of out-coupled ultraviolet light is substantially uniform along the length of the catheter from the proximal end to the distal end;
    a light source capable of providing ultraviolet light having a wavelength in the range of about 320 nm to about 387 nm, optically connected to the catheter in a manner effective to enable irradiation of the catheter body with the ultraviolet light; and
    a power source operably connected to and capable of powering the light source.

44. The implantable catheter system of claim 43, wherein the light source is selected from a mercury lamp, an LED, and a laser.

45. The implantable catheter system of claim 44, wherein the light source is an LED.

46. The implantable catheter system of claim 45, wherein the power source is a battery.

47. The implantable catheter system of claim 43, wherein the power source is wirelessly connected to the light source and capable of powering the light source remotely.

48. The implantable catheter system of claim 47, wherein the power source includes an inductive powering means and the light source includes a corresponding antenna.

49. The implantable catheter system of claim 43, further including an inner photocatalytic layer on the inner surface that undergoes a photocatalysis reaction upon irradiation with ultraviolet light to generate reactive oxygen species.

50. An implantable catheter system, comprising:
    an implantable catheter that can be photocatalytically disinfected without removal from a patient's body, which comprises: an elongate catheter body of predetermined length having a proximal end, a distal end, at least one lumen extending through the catheter body and adapted to transport fluid from the proximal end to the distal end, an outer surface on the exterior of the catheter body, and an inner surface on the interior of the lumen; an inner photocatalytic layer on the inner surface that undergoes a photocatalysis reaction upon irradiation with ultraviolet light to generate reactive oxygen species; an out-coupling means for facilitating out-coupling of ultraviolet light directed into the catheter at the proximal end so that along the length of the catheter a first portion of the light is refracted toward the catheter surfaces and thus toward the inner photocatalytic layer, thereby activating the photocatalysis reaction; wherein the out-coupling means has a density gradient that increases axially along the length of the catheter from the proximal end to the distal end for ensuring that the amount of out-coupled ultraviolet light is substantially uniform along the length of the catheter from the proximal end to the distal end;
    a light source capable of providing ultraviolet light having a wavelength in the range of about 320 nm to about 387 nm, optically connected to the catheter in a manner effective to enable irradiation of the catheter body with the ultraviolet light; and
    a power source operably connected to and capable of powering the light source.

51. A method for inhibiting a biofilm on at least the outer surface of the implantable catheter of claim 1, the method comprising, without removing the implantable catheter from a patient's body, irradiating the catheter body by directing ultraviolet light from a powered light source into the catheter at the proximal end so as to activate the photocatalysis reaction on at least the outer surface of the catheter along the length thereof, thereby generating a biofilm-inhibiting concentration of reactive oxygen species in the localized region of the catheter surface.

52. The method of claim 51, wherein the photocatalytic surfaces of the catheter are irradiated at a power density in the range of about 1 $\mu W/cm^2$ to about 10 $mW/cm^2$.

53. The method of claim 51, wherein the biofilm inhibiting comprises killing microorganisms in a biofilm present or forming on at least the outer surface of the implantable catheter.

54. The method of claim 53, wherein the photocatalytic surfaces of the catheter are irradiated at a power density in the range of about 10 $\mu W/cm^2$ to about 10 $mW/cm^2$.

55. The method of claim 54, wherein the catheter body is irradiated intermittently at approximately regular intervals for a time period in the range of about 2 minutes to about 2 hours.

56. The method of claim 55, wherein the time period is in the range of about 15 minutes to about 1 hour.

57. The method of claim 51, wherein the biofilm inhibiting comprises preventing formation of a biofilm on at least the outer surface of the implantable catheter.

58. The method of claim 57, wherein the photocatalytic surfaces of the catheter are irradiated at a power density in the range of about 1 $\mu W/cm^2$ to about 1 $mW/cm^2$.

59. The method of claim 58, wherein the power density is in the range of about 1 $\mu W/cm^2$ to about 10 $\mu W/cm^2$.

60. The method of claim 59, wherein the catheter body is irradiated continuously over an extended time period of at least 72 hours.

61. The method of claim 51, wherein the powered light source is an ultraviolet LED powered by a battery.

62. The method of claim 51, wherein the powered light source is a UV laser or mercury lamp.

63. The method of claim 51, wherein the method further comprises confirming the presence of a biofilm on at least the outer surface of the catheter prior to irradiating the catheter body.

\* \* \* \* \*